US009211555B2

(12) United States Patent
Meron et al.

(10) Patent No.: US 9,211,555 B2
(45) Date of Patent: Dec. 15, 2015

(54) DEVICE FOR SPRAYING AND/OR MIXING FLUIDS IN PROXIMITY TO A SURFACE

(75) Inventors: Moti Meron, Herzliah (IL); Roee Atlas, Givatayim (IL); Assaf Gershonovitch, Kfar-Saba (IL); Amatzia Gantz, Rehovot (IL); John Goodman, Ann Arbor, MI (US)

(73) Assignees: Ethicon, Inc., Somerville, NJ (US); Omrix Biopharmaceuticals Ltd., Rehovot (IL)

( * ) Notice: Subject to any disclaimer, the term of this patent is extended or adjusted under 35 U.S.C. 154(b) by 661 days.

(21) Appl. No.: 13/484,616

(22) Filed: May 31, 2012

(65) Prior Publication Data

US 2012/0305669 A1 Dec. 6, 2012

Related U.S. Application Data

(60) Provisional application No. 61/493,589, filed on Jun. 6, 2011.

(30) Foreign Application Priority Data

Jun. 5, 2011 (IL) .......................................... 213375

(51) Int. Cl.
  *B05B 7/06* (2006.01)
  *B05B 7/24* (2006.01)
  (Continued)

(52) U.S. Cl.
  CPC ......... *B05B 7/2472* (2013.01); *A61B 17/00491* (2013.01); *A61M 11/00* (2013.01);
  (Continued)

(58) Field of Classification Search
  CPC ........ B05B 7/08; B05B 7/061; B05B 7/2472; B01F 13/0023; B01F 5/0262; A61B 17/00491; A61B 2017/00495; A61B 2017/00522; A61M 15/003; A61M 11/00; A61M 11/02; A61M 11/007
  USPC ......... 239/303, 304, 290, 296, 320, 422–424, 239/428, 433; 604/82, 518
  See application file for complete search history.

(56) References Cited

U.S. PATENT DOCUMENTS

| 4,927,079 A | 5/1990 | Smith |
| 5,152,460 A | 10/1992 | Barty |

(Continued)

FOREIGN PATENT DOCUMENTS

| EP | 1390485 | 10/2006 |
| JP | 11226460 | 8/1999 |

(Continued)

OTHER PUBLICATIONS

International Search Report re: PCT/IL2012/000217 dated Nov. 30, 2012.

*Primary Examiner* — Steven J Ganey

(57) ABSTRACT

The invention relates to an applicator tip for spraying and/or mixing at least two fluids that react together, the tip comprising: at least two fluid conduits for carrying the at least two fluids, each conduit having at least one outlet opening, the openings are positioned substantially on a same plane; at least two gas conduits for carrying a gas volume, each gas conduit comprises a proximal gas tube and a distal gas tube, each distal gas tube is bent as compared to the position of the proximal gas tube, and each distal gas tube has one gas opening positioned distal from the plane of the outlet openings; and a housing for accommodating the at least two fluid conduits and the at least two gas conduits. The device allows efficient spraying in close proximity to a surface.

36 Claims, 11 Drawing Sheets

(51) Int. Cl.
*A61B 17/00* (2006.01)
*B01F 5/02* (2006.01)
*B01F 13/00* (2006.01)
*B05B 7/08* (2006.01)
*A61M 11/00* (2006.01)
*A61M 15/00* (2006.01)
*A61M 11/02* (2006.01)
*A61M 35/00* (2006.01)

(52) U.S. Cl.
CPC ............ *A61M 11/007* (2013.01); *A61M 11/02* (2013.01); *A61M 15/0003* (2013.01); *A61M 35/003* (2013.01); *B01F 5/0262* (2013.01); *B01F 13/0023* (2013.01); *B05B 7/061* (2013.01); *B05B 7/08* (2013.01); *A61B 2017/00495* (2013.01); *A61B 2017/00522* (2013.01)

(56) References Cited

U.S. PATENT DOCUMENTS

| | | | |
|---|---|---|---|
| 5,526,981 | A | 6/1996 | Sanson |
| 6,121,232 | A | 9/2000 | Nur et al. |
| 6,432,084 | B1 | 8/2002 | Levinson et al. |
| 6,547,161 | B1 | 4/2003 | Huang |
| 6,612,506 | B1 | 9/2003 | Huang |
| 7,125,569 | B2 | 10/2006 | Nur et al. |
| 7,163,160 | B2 | 1/2007 | Liu |
| 7,694,944 | B2 | 4/2010 | Gottlieb et al. |
| 8,033,483 | B2 * | 10/2011 | Fortier et al. ................ 239/303 |
| 2009/0108091 | A1 | 4/2009 | Steffen |
| 2009/0234326 | A1 * | 9/2009 | Hayakawa ................... 604/82 |
| 2010/0270401 | A1 | 10/2010 | Charpie et al. |

FOREIGN PATENT DOCUMENTS

| | | |
|---|---|---|
| JP | 2001/321441 | 11/2001 |
| JP | 2003/211063 | 7/2003 |
| JP | 2008/295834 | 12/2008 |
| JP | 2011/194304 | 10/2011 |
| WO | WO 98/10703 | 3/1998 |
| WO | WO 98/33533 | 8/1998 |
| WO | WO 02/095019 | 11/2002 |
| WO | WO 2007/059801 | 5/2007 |

* cited by examiner

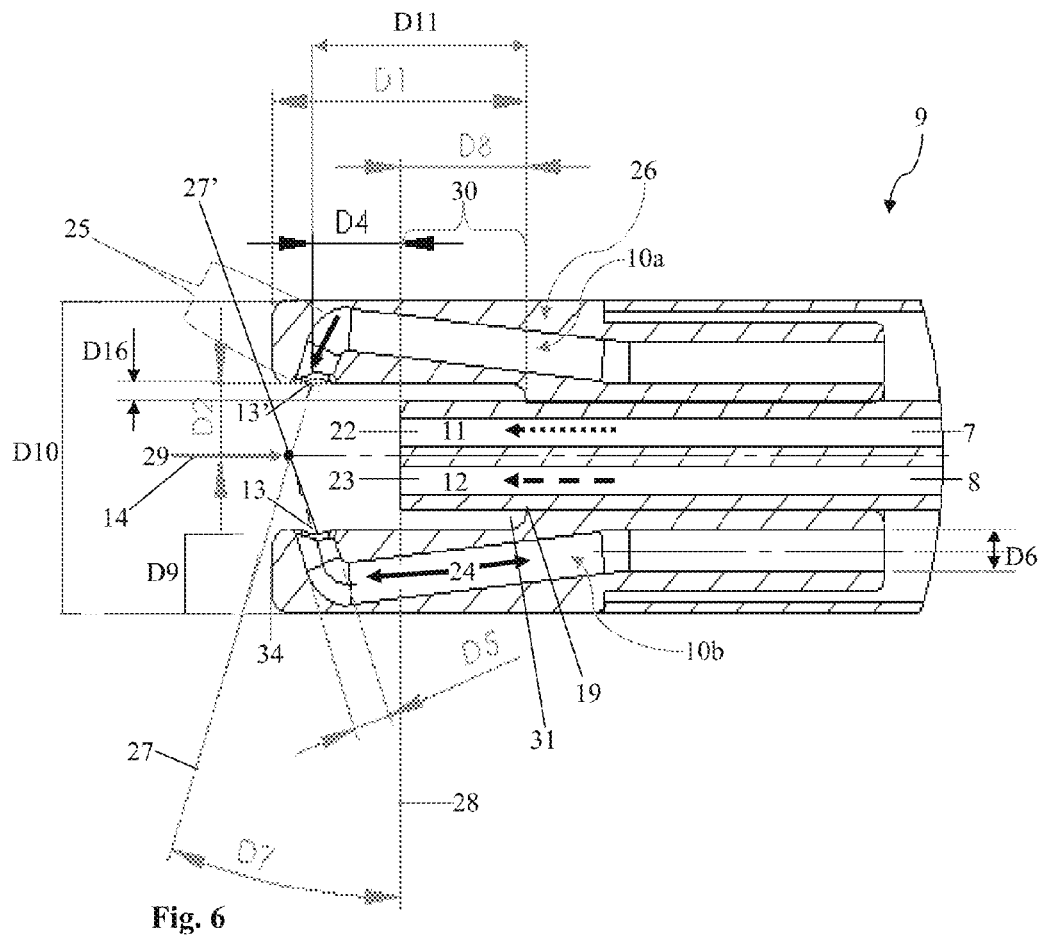
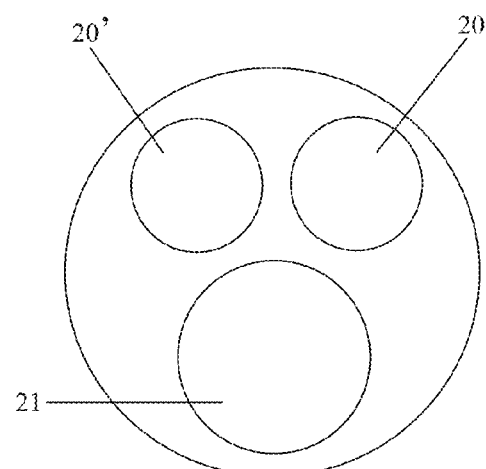
Fig. 6
Fig. 7

DEVICE FOR SPRAYING AND/OR MIXING FLUIDS IN PROXIMITY TO A SURFACE

FIELD OF THE INVENTION

The invention relates to an applicator tip suitable for use with an applicator device for spraying and/or mixing a multi-component fluid.

BACKGROUND OF THE INVENTION

Devices for spraying fluids are basically known from U.S. Pat. No. 7,694,944; U.S. Pat. No. 5,152,460; U.S. Pat. No. 6,547,161; U.S. Pat. No. 6,612,506; U.S. Pat. No. 5,526,981 and U.S. Pat. No. 7,163,160.

In particular, medical devices for spraying at least two fluid components which react together rapidly are known from U.S. Pat. No. 6,432,084; and US 20090108091.

The above publications are silent on the performance of the medical devices when spraying is carried out in close proximity to the target location. There is a need for a medical device for spraying two components, which react together rapidly, in close proximity to a target surface.

SUMMARY OF THE INVENTION

In one aspect, the invention relates to an applicator tip for spraying and/or mixing at least two fluids that react together, the tip comprising: at least two fluid conduits for carrying the at least two fluids, each conduit having at least one outlet opening positioned substantially on a same plane; at least two gas conduits for carrying a gas volume, each gas conduit comprises a proximal gas tube and a distal gas tube, wherein each distal gas tube is bent as compared to the position of the proximal gas tube, and wherein each distal gas tube has one gas opening with a diameter positioned distal from the plane of the outlet openings; and a housing for accommodating the at least two fluid conduits and the at least two gas conduits.

In one embodiment of the invention, the proximal and distal gas tubes are a one part unit.

In one embodiment of the invention, an axis of the distal gas tube forms an angle with respect to the plane of the outlet openings that is less than 90°.

In one embodiment of the invention, the angle is in the range of 15°-35°, 15°-25° or 15°-20°. In another embodiment of the invention, the angle is about 20°.

In one embodiment of the invention, the axis of the distal gas tubes intersect at a common point located distal from the plane of the outlet openings.

In one embodiment of the invention, the ratio between a vertical distance from a center line of the tip to the gas opening and a vertical distance from the plane where the outlet openings are positioned to a center point of the gas opening is in the range of 0.8-1.75.

In one embodiment of the invention, the ratio between the vertical distance from the center line of the tip to the gas opening and the diameter of the gas opening is in the range 0.9-3.5 or in the range of 1-2.

In one embodiment of the invention, the diameter of the gas opening is in the range of higher than 0.4 to lower than 1.1 mm or in the range of 0.7-0.9 mm.

In one embodiment of the invention, the gas opening has an area in the range of higher than $0.125$ $cm^2$ to lower than $0.950$ $cm^2$ or in the range of $0.385$ $cm^2$-$0.636$ $cm^2$.

In one embodiment of the invention, the housing comprises a base plate from which the fluid conduits and the proximal gas tubes extend through.

In one embodiment of the invention, the plane where the outlet openings are positioned is elevated from the base plate by a conduit extension so that at least two recesses are formed between the conduit extension and the proximal gas tubes.

In one embodiment of the invention, the conduit extension is an elongation of the at least two fluid conduits.

In one embodiment of the invention, the ratio between a vertical distance from the plane where the outlet openings are positioned to a center point of the gas opening and a vertical distance from the base plate to the plane where the outlet openings are positioned is in the range of 0.19-0.50 or in the range of 0.235-0.400.

In one embodiment of the invention, the ratio between the vertical distance from the base plate to the plane where the outlet openings are positioned and a vertical distance from the base plate to a center point of the gas outlet opening is in the range of 0.71-0.81.

In one embodiment of the invention, the ratio between a vertical distance from the center line of the tip to the gas opening and the width of the recess is in the range of 2.5-14.

In one embodiment of the invention, the distance from the base plate to the plane where the outlet openings are positioned is in a range of 3.0-3.4 mm.

In one embodiment of the invention, the recess has a depth in a range of 3.0-3.4 mm.

In another embodiment of the invention, the recess has a width in a range of 0.10-0.40 mm.

In one embodiment of the invention, the tip comprises two fluid conduits arranged side by side, and the recess has a width in a range of 0.30-0.35 mm.

In one embodiment of the invention, the tip comprises two fluid conduits arranged concentrically, and the recess has a width in a range of 0.100-0.150 mm.

In one embodiment of the invention, the vertical distance from the base plate to a distant point of the tip is in the range of 4.0-5.0 mm.

In one embodiment of the invention, the overall diameter of the tip is in the range of 4.8-12 mm.

In one embodiment of the invention, the housing comprises at least two structures for encapsulating at least a part of the gas conduit, wherein the structures emerge from the base plate.

In one embodiment of the invention, the housing comprises a structure for encapsulating the conduit extension.

In one embodiment of the invention, the recess is formed between the housing encapsulating the gas conduit and the housing encapsulating the conduit extension.

In such an embodiment, the tip can have one or more of the following characteristics: a recess having a depth in a range of 3.0-3.4 mm; a recess having a width in a range of 0.10-0.40 mm; two fluid conduits arranged side by side, and a recess having a width in a range of 0.30-0.35 mm; two fluid conduits arranged concentrically, and a recess having a width in a range of 0.100-0.150 mm.

In one embodiment of the invention, the at least two fluid conduits are symmetrically arranged with respect to the center line of the tip.

In one embodiment of the invention, the tip comprises two fluid conduits arranged side by side.

In one embodiment of the invention, the tip comprises two fluid conduits arranged concentrically.

In one embodiment of the invention, one of the fluid conduits has two outlet openings and the other fluid conduit has one outlet opening.

In one embodiment of the invention, one of the fluids comprises thrombin and the other comprises fibrinogen.

In one embodiment of the invention, the tip is for use at an inlet gas pressure in the range of 10-20 psi or in the range of 15-20 psi.

In one embodiment of the invention, the tip is for use at an inlet gas flow in the range of 2.8 to 6 L/min or in the range of 4.4 to 6 L/min.

In one embodiment of the invention, the tip is for use from a close proximity to a target spraying area, wherein the distance between the distant point of the tip and the target is less than 10 cm, less than 6 cm, in the range of 1-5 cm, 2-4 cm, 2-3 cm or in the range of 1-2 cm.

Advantageously, the applicator tip according to the invention allows efficient spraying in close proximity to a surface.

BRIEF DESCRIPTION OF THE DRAWINGS

The features, aspects, and advantages of the present invention will become better understood with regard to the following description, examples, claims, and the following figures.

FIG. 1 shows an external view of an applicator tip (9) connected to an applicator device (2) according to some embodiments of the present invention.

FIG. 2 shows an external view of an applicator tip (9) according to some embodiments of the present invention.

FIG. 3 shows a cross-sectional view of the applicator tip (9) according to some embodiments of the present invention.

FIG. 4 shows an enlarged view of the tubing arrangement seen in area A of FIG. 3 where the fluid conduits (11, 12) are arranged side by side according to some embodiments of the present invention.

FIG. 5 shows an enlarged view of the of the applicator tip (9, seen in area B of FIG. 3) according to some embodiments of the present invention. The Fig. shows outlet openings of the first and second liquid components (22, 23) at the end of the fluid conduits (11, 12) that are arranged side by side; and two gas outlet openings (13 and 13'). The two openings of the liquid component (22, 23) are located on the same level surface of base 19.

FIG. 6 shows an enlarged cross-sectional view of the applicator tip (9) wherein the openings of the two fluid conduits (22, 23) protrude above the level surface of base 19 according to some embodiments of the present invention.

FIG. 7 shows an enlarged frontal view of a control applicator tip used in the Examples below having two parallel fluid conduits with two outlet openings (20, 20'), and a gas conduit having one outlet opening (21). All three openings are located on the same surface plane.

FIGS. 8A and 8B show black and white pictures of a 20 $cm^2$ surface area sprayed with fibrin sealant, at a short distance of 3-4 cm from the surface, (A) using an applicator tip according to FIG. 5 or (B) the control applicator tip shown in FIG. 7. The arrows in FIG. 8B mark the localization of uncovered regions.

FIG. 9 shows a graph plotting the spraying distance from the middle point of an "X" mark (target) against the diameter of an area uncovered with fibrin sealant. Spraying was carried out with an applicator tip according to FIG. 5 or the control applicator tip shown in FIG. 7.

FIGS. 10A and 10B show representative pictures of an experiment carried out in a similar manner to the experiment described in FIG. 9. Spraying of fibrin sealant was carried out at a distance of 3-4 cm from the "X" mark target. Spraying was carried out with (A) the applicator tip according to FIG. 5 or (B) with the control applicator tip. The arrow in FIG. 10B shows the diameter of the uncovered area.

FIG. 11 shows a graph plotting the spraying distance from the middle point of a surface against the diameter of the un-covered area. The experiment was carried out with applicator tips having an angle of the distal gas outlet openings (see angle D7 in FIG. 5) of 20° or 35°.

FIGS. 12A-F show representative pictures of the formed clots using the different applicator tips and under the different spraying distances: FIGS. A, B correspond to spraying with a tip shown in FIG. 5 having D7 angle of 20°. FIGS. C, D correspond to spraying with a tip shown in FIG. 5 having an increased D7 angle of 35°. FIGS. E, F correspond to spraying with a control tip having no D7 angle. FIGS. B, D and F correspond to spraying from a distance of 2-3 cm and FIGS. A, C, and E correspond to spraying from a shorter distance of 1-2 cm. The arrows in the Figs. show the diameter of the uncovered area.

FIG. 13 shows an external view of an applicator tip (9) connected to an applicator device (2), the applicator tip has two fluid conduits (22, 23, 22') in a concentric arrangement (shown best in FIGS. 16A-16C) according to some embodiments of the present invention. FIGS. 14A-14C show different views of the applicator tip (9) with the two fluid conduits in a concentric arrangement shown in FIG. 13 according to some embodiments of the present invention. FIG. 14A shows an upper view of the tip at the end of a manifold; FIG. 14B shows a sided view of the tip at the end of a manifold; FIG. 14C shows an upper cross sectional view of the tip at the end of a manifold. In FIG. 14C encircled are the applicator tip (9; Area D) and the tubing arrangement in the manifold (Area C).

FIG. 15 shows an enlarged view of the fluid tubing arrangement seen in Area C of FIG. 14C.

FIGS. 16A-16C show a tip with concentric tubing arrangement according to some embodiments of the invention. FIG. 16A shows an enlarged view of area D seen in FIG. 14C according to some embodiments of the present invention. FIG. 16B shows a frontal view of the applicator tip (9) seen in FIG. 14C. FIG. 16C shows an enlarged sided view of the applicator tip (9) showing structures of the housing (26) according to some embodiments of the present invention: structure 19—is a base plate from which the fluid conduits and the proximal gas tubes extend through; structures 33*a*, 33*b* that emerge from the base plate and encapsulate the gas conduit; and structure 35 that encapsulate the conduit extension (30).

FIGS. 17A-17B show two different types of fluid tubing arrangements. A—shows a frontal view of the fluid tubing arrangement in FIG. 5 according to some embodiments of the present invention. The tubing is arranged side by side; B—shows a frontal view of the fluid tubing arrangement in FIG. 16 according to some embodiments of the present invention. The tubing is arranged concentrically.

FIG. 18 shows a graph plotting the protrusion level of the fluid conduit openings above surface base 19 against the volume administered until a change in the spray pattern was observed.

FIG. 19 show four transparent square sheets having an area of 100, 25, 9, and 4 $cm^2$ piled with the 4 $cm^2$ sheet being on top. The sheets are aligned according to their center point. The piled sheets were used in an experiment aimed to determine the fibrin dispersion pattern around a target location following spraying with the applicator tip according to the invention (as shown in FIG. 16) (at a short distance of 1-2 cm form the target and at a pressure of 15-20 psi or at a short distance of 5 cm form the target and at a pressure of 15 psi) and the control tip shown in FIG. 7 (at a distance of 10 or 15 cm form the target at a pressure of 25 psi—according to the manufacturer recommendation). The exposed distance of the x-axis from the center point of all the sheets (shown by the black arrows) was 0-1 cm, 1-1.5 cm, 1.5-2.5 cm, and 2.5-5 cm for the 4, 9, 25, and 100 cm² sheets, respectively.

DETAILED DESCRIPTION OF THE INVENTION

In one aspect, the invention relates to an applicator tip for spraying and/or mixing at least two fluids. Advantageously, the tip's special geometric design enables use of the tip for short distance (from the target area) spraying of at least two fluid components which react together rapidly. Typically, the term "at least two fluids" relates to any biological (e.g. fluids which derive from living organisms or manufactured by recombinant technology) and/or chemical fluids (e.g. fluids which are chemically synthesized). The at least two fluids can be at least two components which react together rapidly and form a polymer which can clog the applicator tip. Non limiting examples of two fluids are fibrinogen comprising component and thrombin comprising component; alginate and calcium; chondroitin sulphate and an acid such as hyaluronic acid; antigen and adjuvant; two components which form a colloidal suspension; two components which enables the formation of liposomes; two components in which one requires activation by the other; two components in which one component will activate the other component.

In one embodiment of the invention the fluids react to form a polymer within a few milliseconds and up to a few minutes.

The invention provides an applicator tip for spraying and/or mixing at least two fluids that react together. The tip comprises: at least two fluid conduits for carrying the at least two fluids, each conduit having at least one outlet opening positioned substantially on a same plane; at least two gas conduits for carrying a gas volume, each gas conduit comprises a proximal gas tube and a distal gas tube, wherein each distal gas tube is bent as compared to the position of the proximal gas tube, and wherein each distal gas tube has one gas opening with a diameter and positioned distal from the plane of the fluids outlet openings; and a housing for accommodating the at least two fluid conduits and the at least two gas conduits.

Figure 5:
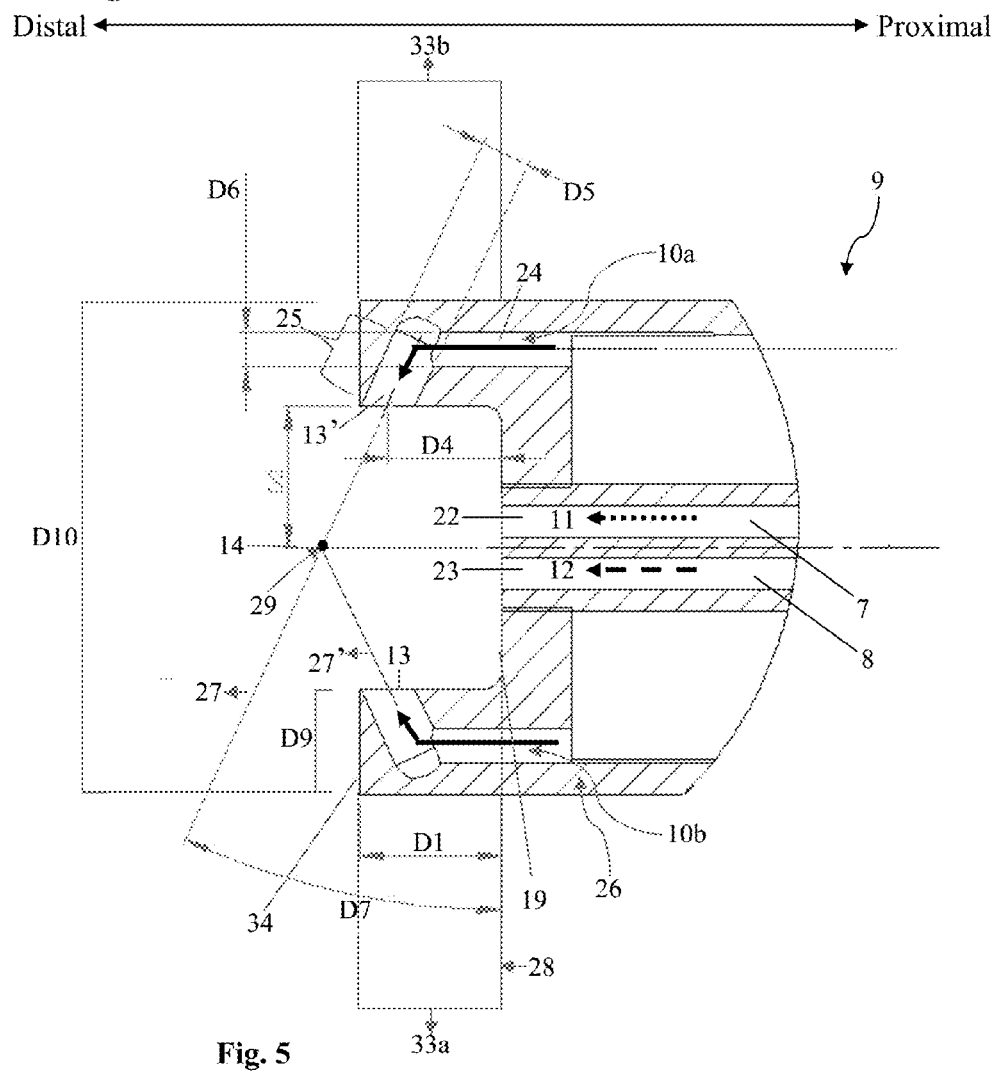

FIG. 5 shows a tip (9) according to one embodiment of the invention. The Fig. shows two fluid conduits (11, 12) for carrying two fluids and two outlet openings (22 and 23) positioned substantially on a same plane (28). The Fig. also shows two gas conduits (10a, 10b) for carrying a gas volume. Each gas conduit comprises a proximal gas tube (24) and a distal gas tube (25). The distal gas tube (25) is bent as compared to the position of the proximal gas tube. Each distal gas tube has one gas opening (13, 13') having a diameter D5. The gas opening is positioned distal from the plane (28), where the outlet openings (22, 23) are located. The tip comprises a housing (26) for accommodating the two fluid conduits and the two gas conduits.

In contrast to the geometry of control tips, the geometry of the tip according to the invention allows, when spraying from a short distance from the target area two fluid components which react together rapidly, obtaining superior mixing of the fluids and more homogeneously and complete covering of the sprayed area (see FIGS. 8, 9, 10, 11, 12, 20).

Figure 16A:
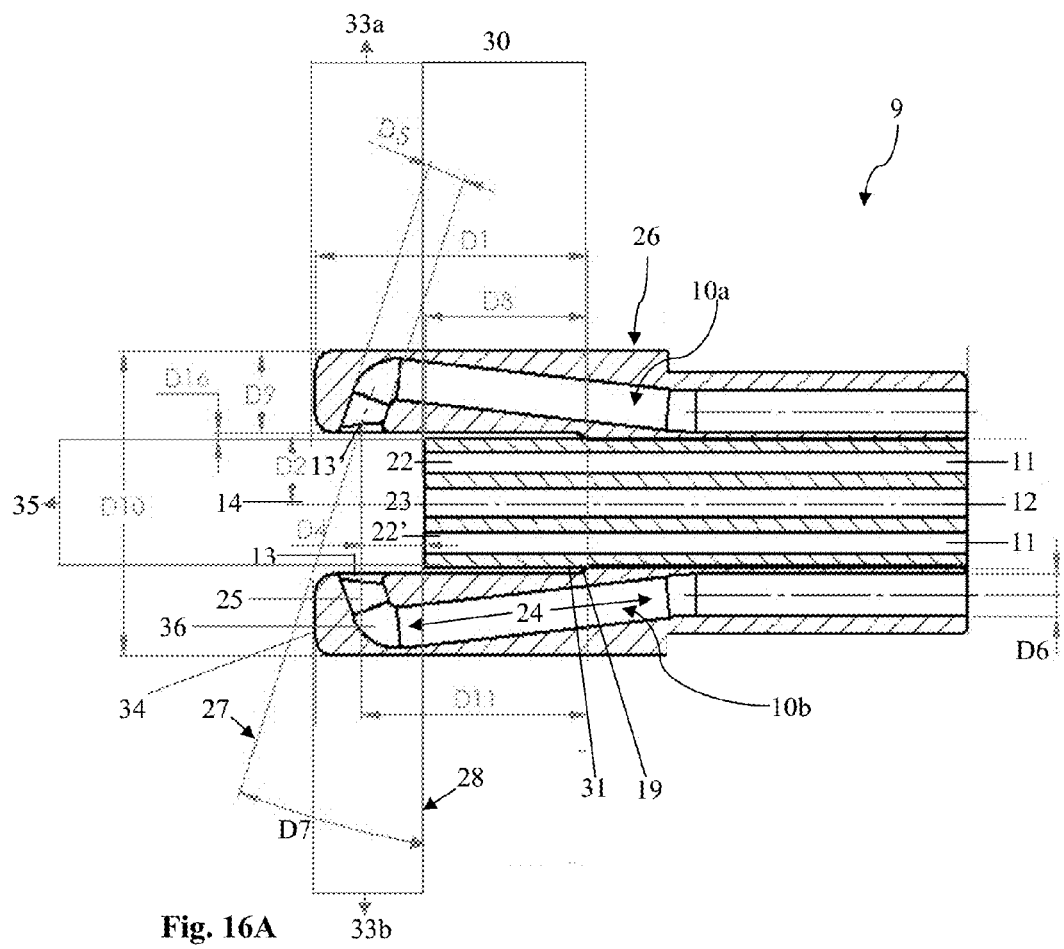
Figure 16B:
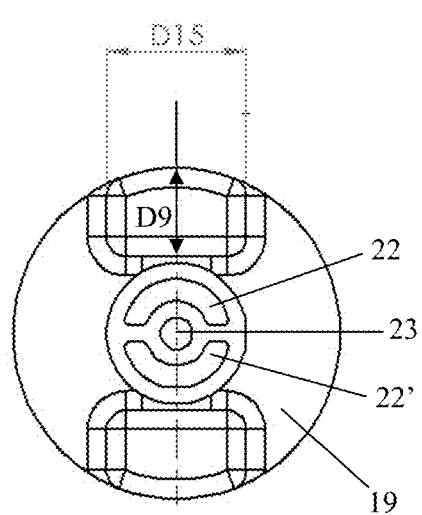

In one embodiment of the invention, the proximal and distal gas tubes are formed from a one part unit that is bent. In another embodiment of the invention, the proximal gas tube and the distal gas tubes are two tubes which are directly connected or sealed (E.g. as shown in FIG. 5). In another embodiment of the invention, the proximal and distal tubes are indirectly connected e.g. by a curved tube (36; E.g. as shown in FIG. 16A).

In one embodiment of the invention, as shown in FIGS. 5 and 6, an axis (27) of the distal gas tube (25) forms an angle (D7) with respect to the plane (28) of the outlet openings that is less than 90° such as is in the range of 15°-35°, 15°-25° or 15°-20°. An optimal D7 angle was found to be an angle of less than 35°, e.g. an angle of 20° (see FIGS. 11 and 12).

In one embodiment of the invention, as shown in FIGS. 5 and 6, the tip comprises axis of the distal gas tubes 27 and 27' which intersect at a common point (29). The intersect point (29) is located distal from the plane of the liquid outlet openings (28).

In one embodiment of the invention, the tip of the invention has a ratio between a vertical distance (FIGS. 5, 6 and 16A, D2) from a center line of the tip (14) to the gas opening (13) and a vertical distance (D4) from the plane where the outlet openings are positioned to a center point of the gas opening in the range of 0.8-1.75. In one embodiment of the invention, distance D2 is in the range of 1-1.4 mm such as 1.2 mm.

In one embodiment of the invention, distance D4 is in the range of 0.8-1.2 mm such as 0.8 mm.

In another embodiment of the invention, the tip of the invention has a ratio between D2 (FIGS. 5, 6 and 16A) and the diameter (D5) of the gas opening in the range 0.9-3.5 or in the range of 1-2.

The diameter of the gas opening (D5) can be in the range of higher than 0.4 to lower than 1.1 mm or in the range of 0.7-0.9 mm.

The area of the gas opening in a tip (9) of the invention can be in the range of higher than 0.125 cm² to lower than 0.950 cm² e.g. in the range of 0.385 cm² to 0.636 cm².

As shown in one embodiment of the invention (e.g. FIGS. 5, 6 and 16A-C), the housing comprises a base plate/surface base (19) from which the fluid conduits and the proximal gas tubes extend through.

Figure 16C:
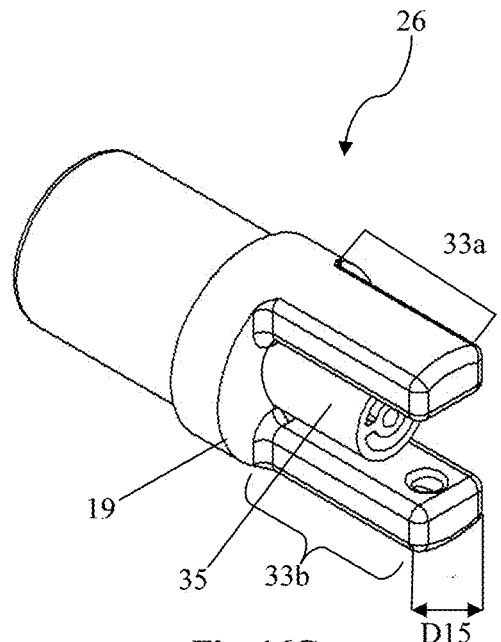

In a tip of one embodiment of the invention (FIGS. 6 and 16A) the plane (28) where the outlet openings (22, 23 or 22, 22', 23) are positioned, is elevated from the base plate (19) by a conduit extension (30) so that at least two recesses (31) are formed between the conduit extension (30) and the proximal gas tubes (24). In one embodiment of the invention, the liquid outlet openings are elevated from the base plate by extension of the two fluid conduits that protrude from the base plate (19). This elevation or protrusion of the outlet openings from the base plate create recesses limited by the conduit extension and the proximal gas tubes. In one embodiment of the invention, the conduit extension and the gas tubes are encapsulated by and/or are accommodated within a housing (e.g. as shown in FIG. 16C). In such embodiments, the recesses are limited by the housing encapsulating and/or accommodating the conduit extension and the housing encapsulating and/or accommodating the proximal gas tubes.

In one embodiment of the invention, the conduit extension (30) is obtained by an elongation of the at least two fluid conduits.

In one embodiment of the invention, the ratio between (D4 in FIG. 6) a vertical distance from the plane (28) to a center point of the gas opening (13) and a vertical distance (D8) from the base plate (19) to the plane where the outlet openings are positioned is in the range of 0.19-0.50 or in the range of 0.235-0.400.

In one embodiment of the tip of the invention, the ratio between D8 and D11 (see in FIGS. 6 and 16A) [the vertical distance from the base plate (19) to a center point of the gas outlet opening] is in the range of 0.71-0.81.

In one embodiment of the invention, the ratio between distance D2 and D16 [the width of the recess (31)] (D16 in FIGS. 6 and 16A) is in the range of 2.5-14, in the range of 2.86-4.67 or in the range of 6.67-12.6.

In the tip according to one embodiment of the invention, the distance D11 is in the range of 3.2-5.4 mm, in the range of 3.8-4.6 mm or 4.2 mm. In the tip according to one embodiment of the invention, the distance D8 and/or the depth of the recess (31 in FIGS. 6, and 16A) is in the range of 2.4-4.2 mm or in the range of 3.0-3.4 mm. The recess (31) can have a width (D16) in a range of 0.10-0.40 mm. In one embodiment of the invention, the tip comprises two fluid conduits arranged side by side and the recess (31) has a width (D16) in a range of 0.30-0.35 mm. In another embodiment of the invention, the tip comprises two fluid conduits arranged concentrically and the recess (31) has a width (D16) in a range of 0.100-0.150 mm.

In one embodiment of the invention, the vertical distance (D1 in FIGS. 5, 6 and 16A) from the base plate (19) to a distant point of the tip (34) is in the range of 1.4-5.0 mm or in the range of 4.0 to 5.0 mm.

In one embodiment of the invention, the overall diameter of the tip (D10 in FIGS. 5, 6 and 16A) is in the range of 4.8-12 mm.

In one embodiment of the invention, the distance (D9 in FIGS. 5, 6, 16A and 16B) from the plane where the gas opening (13) is positioned to the outer wall of the structure that encapsulates the gas conduit (33a and b) is in the range of 0.6-1.5 mm e.g. 1.38 mm.

In one embodiment of the invention, the width (D15 in FIGS. 16B and 16C) of the structure (33a and 33b) that encapsulates the gas conduit is in the range of 0.6-3 mm e.g. 2.2 mm.

In the case that the gas conduit is not encapsulated by a housing structure (33a and b), dimensions D9 and D15 are of the gas conduit dimensions.

In one embodiment of the invention, the housing comprises at least two encapsulating structures (33a and 33b e.g. in FIGS. 5, 16A 16C) emerging from the base plate (19) for encapsulating at least a part of the gas conduit and/or the housing comprises a structure (35) for encapsulating at least a part of the conduit extension. In such an embodiment, the recess (31) is formed between the structure encapsulating the gas conduit and the structure encapsulating the conduit extension. The recess (31) can have a depth in a range of 2.4-4.2 mm or 3-3.4 mm; and a width (D16) in the range of 0.10-0.40 mm. In one embodiment, the tip comprises two fluid conduits arranged side by side and the recess (31) has a width (D16) in a range of 0.30-0.35 mm. In another embodiment, the tip comprises two fluid conduits arranged concentrically and the recess (31) has a width (D16) in a range of 0.100-0.150 mm.

The tip according to one embodiment of the invention has at least two fluid conduits (11 and 12) which are symmetrically arranged with respect to the center line of the tip (14).

The tip according to the invention can have two or more fluid conduits. In one embodiment of the invention each conduit has one outlet opening as in conduits that are arranged side by side (22, 23 in FIG. 17A). In another embodiment, the tip comprises two fluid conduits which are arranged concentrically and one fluid conduit has two openings (23 and 23' in FIG. 17B).

In one embodiment of the invention, the tip is used for spraying and/or mixing two fluids e.g. a biological fluid comprising thrombin and a biological fluid comprising fibrinogen. In certain embodiments, one of the fluids is a biological fluid and the other is not. In further embodiments, both fluids are not biological fluids but react together.

The tip according to certain embodiments is for use at an inlet gas pressure in the range of 10-20 psi or in the range of 15-20 psi. The tip according to certain embodiments is for use at an inlet gas flow in the range of 2.8 to 6 L/min or in the range of 4.4 to 6 L/min.

Advantageously, the tip according to the invention can be used from a short distance or close proximity to a target spraying area. One such short distance between the distant point of the tip (34) and the target area is less than 10 cm, less than 6 cm, in the range of 1-5 cm, 2-4 cm, 2-3 cm or in the range of 1-2 cm.

The term "short distance" or "close proximity" from a target refers to a distance range of less than 10 cm from the target down to the closest possible distance in which there is no contact between the tip and the target area. The distance can be less than 6 cm, in the range of 1-5 cm, 2-4 cm, 2-3 cm 1-2 cm. For example, the distance can be 9, 8, 7, 6, 5, 4, 3, 2, 1, 0.5 cm from the target.

The applicator tip comprises a housing (26) encapsulating at least part of the at least two fluid conduits, and at least part of the at least two gas tubes. The at least two fluid conduits having a length, a proximal end (at the rear part of the applicator tip), and a distal end (at the front part of the applicator tip). The distal end of the gas tube has at least two distal openings each having an inner diameter and located distal to the distal end of the at least two fluid conduits.

The term "an applicator tip" is oftentimes interchangeable with the term "device".

In one embodiment of the invention, the at least two distal openings of the gas conduit are positioned such that they are facing each other substantially towards one another ("opposing openings").

In another embodiment of the invention, the openings of the gas tube are aligned such that gas that flows through the openings intersects at a common point (29) (see FIGS. 5 and 6).

The applicator tip is suitable for use with an applicator device for spraying a multi-component fluid e.g. a component comprising at least two fluids such as a first and a second component of a fibrin sealant. In one embodiment of the present invention, the first component comprises fibrinogen and the second component comprises thrombin.

Figure 1:
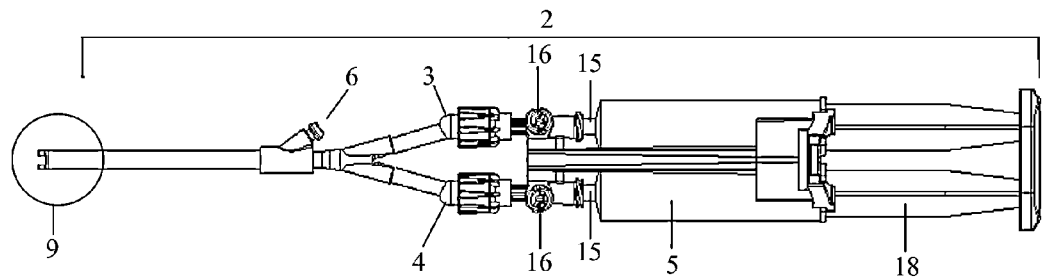
Figure 2:
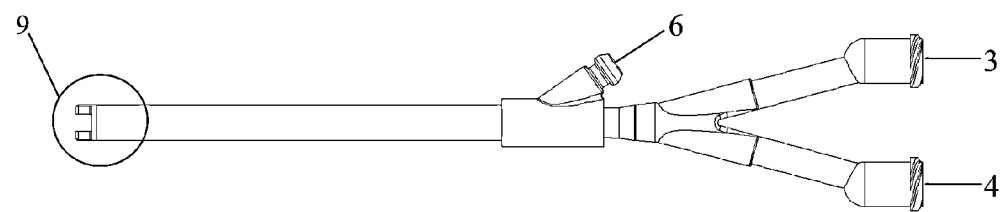

FIGS. 1 and 2 show an external view of one embodiment of the applicator tip (9). In FIG. 1 the applicator tip (9) is connected to an applicator device (e.g. as described in WO 2007059801 wherein the applicator tip according to the invention is at the end of a manifold structure).

In one embodiment of the invention, the applicator tip comprises a first and second port (3, 4 in FIGS. 1 and 2) that are in fluid communication with the outlet ends of the supply containers (15 in FIG. 1) of the applicator device (2). The connection between the first and second port and the applicator device (2) can be by luer lock connecters.

The outlets of the supply containers (15) can be directly attached to the first and second ports (3, 4) or can be indirectly attached e.g. by employing fluid control devices as described in WO9810703 (feature 148 in FIG. 1 of WO9810703; feature 16 in FIG. 1 of the instant application) arranged between the outlets (15) and the ports (3, 4).

Figure 14A:
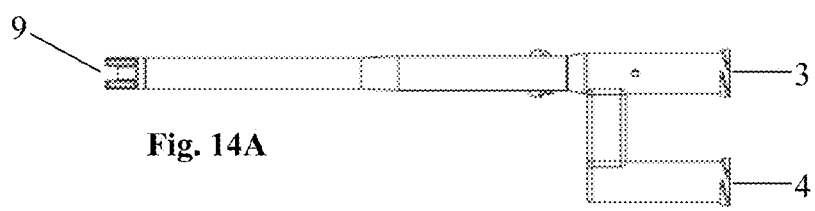
Figure 14B:
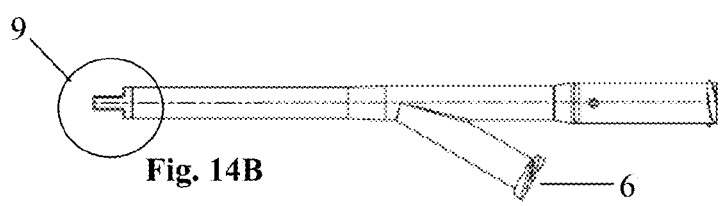
Figure 14C:
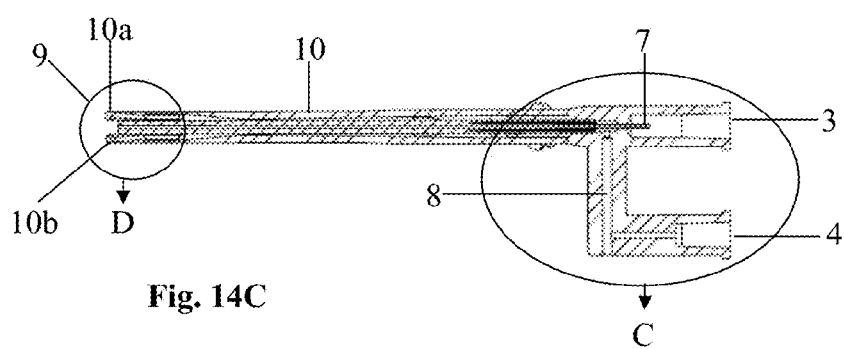

In order to spray the multi-component fluid, the applicator tip comprises at least one gas inlet port (6 in FIGS. 1, 2 and 14B) and at least two gas openings (13 and 13' in FIGS. 5, 6, and 16A) for providing a gaseous substance (e.g. air, $N_2$, $CO_2$ or other medical gases like oxygen) to the applicator tip (9). In FIGS. 1-3, 5 6 and 16A, two opposing outlet gas openings are provided in the applicator tip (9).

Figure 3:
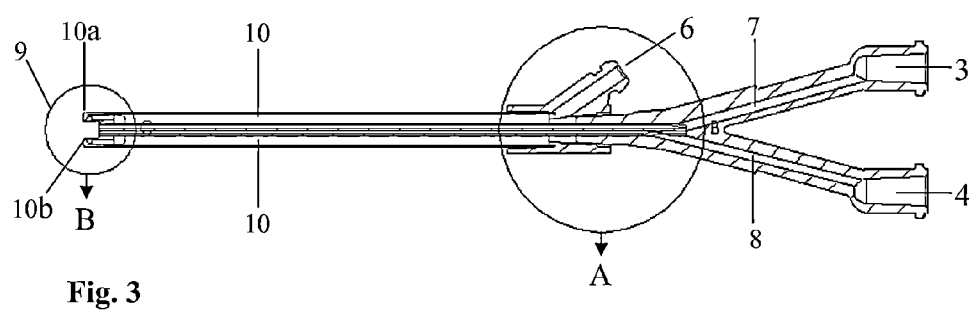
Figure 4:
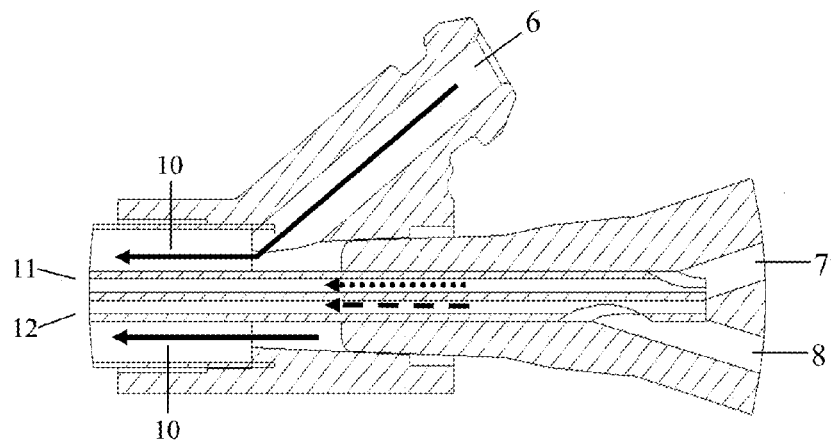

FIGS. 3 and 5 show an embodiment of a cross-sectional view of the applicator tip (9).

In one embodiment of the invention, the applicator tip comprises a housing for accommodating at least part of the two fluid conduits and at least part of the gas tube. In another embodiment of the invention, the applicator tip comprises a recess (31 in FIGS. 6 and 16A) separating the proximal gas tube and the openings of the fluid conduits. In one embodiment of the present invention, two internal tubes (7 and 8 for delivering the first and second fluid components to the applicator tip (9) extend from the first and second ports (3, 4) up to the two fluid conduits (11, 12). In one embodiment of the invention, the fluid conduits are symmetrically arranged with respect to the center line of the applicator tip (14, shown in FIGS. 5, 6 and 16A). In one embodiment of the invention, the fluid conduits are symmetrically arranged with respect to a longitudinal axis (14).

The distal fluid conduit openings (22, 22', 23) are substantially coplanar (e.g. located on the same plane) and the biological fluids are substantially simultaneously released from the distal openings out of substantially parallel release axis for allowing them to react with one another.

At least a part of the fluid conduits can be arranged side by side (e.g. as seen in FIG. 3-6, 17A) or concentrically (FIG. 13-16, 17B). Also, the applicator tip can comprise at least one gas tube (10) extending from the gas inlet port (6) up to the distal end of the applicator tip (9). The gas tube can be arranged concentrically to the internal tubes of the fluid components e.g. the internal tubes of the first and second components (7, 8). In an alternative embodiment, the applicator tip comprises several gas tubes which are located at least partially parallel to the fluid conduits.

In one embodiment of the invention, the applicator tip comprises two fluid conduits which are arranged next to each other and one gas conduit which is arranged concentrically to the two fluid conduits (as seen in FIG. 4, which shows an enlarged cross-sectional view of the tubing arrangement seen in area A of FIG. 3). The fluid path of the first and second components is marked by doted and fragmented arrows; the gas fluid path is marked by continuous arrows (see the arrows in FIGS. 4 and 5).

Typically, the fluid flow out from the fluid openings of the applicator tip is not due to "Venturi Effect" caused by gas assistance but as a result of the plunger's movement (the plunger are shown as feature 18 in FIGS. 1 and 13) which displaces the liquid contained in the supply containers (5) of the applicator device (2).

In another embodiment of the invention, the applicator tip comprises two distal openings for delivering the liquid components which are located next to each other (see 22 and 23 in FIG. 5), and two opposing distal openings for delivering the gas (see 13 and 13' in FIG. 5).

Advantageously, the volume of the fluid components such as fibrin sealant delivered through the openings of the fluid conduits is regulated via movement of the plungers (18) actuated by the user of the device. Thus, in one embodiment of the invention, the applicator tip does not comprise a needle valve which acts to control the liquid/fluid flow out from the openings of the fluid conduits.

FIG. 5 shows an enlarged cross-sectional view of the applicator tip (19) (seen in area B of FIG. 3). In FIG. 5, the two openings of the fluid conduits are located at the same level as the surface of base plate 19 i.e. overlapping exists between base plate 19 and plane 28 where the outlet openings (22, 23) are positioned. FIG. 6 shows a cross-sectional view of another embodiment of the applicator tip (9) wherein the openings of the two fluid conduits (22, 23) protrude above the level surface of base plate 19 forming a recess (31) between the protrusion and the proximal gas tubes (24). The distance of the openings (22, 23) located at the distal end of the fluid conduits (11 and 12) from the level of the base plate (19) can be in the range of 2.4-4.2 mm (see distance D8 in FIGS. 6 and 16A). In one embodiment of the invention, the distance of the openings (22, 23) at distal end of the fluid conduits (11 and 12) from the level surface of the base is in the range of 3-3.4 mm. As the outlet opening of the fluid conduits are distant from the housing surface base (19), accumulation of clogged fluid components nearby the openings and blockage of the openings is prevented. Accordingly, the tip shown in FIGS. 6 and 16A is superior to the tip shown in FIG. 5 due to the fact that it allows efficient spray for a prolonged period of time.

An identical distance between each gas outlet opening (13 or 13') and the longitudinal center line of the applicator tip (14) is of advantage. In one embodiment of the invention, the distance between each gas outlet opening and the longitudinal center line of the applicator tip (14) is in the range of 1-1.4 mm (see distance D2 shown in FIGS. 5 and 6). The term "longitudinal center line of the applicator tip" refers to an imaginary center line made completely through the applicator tip e.g. line 14 as exemplified in FIGS. 5, 6 and 16A. The oblique position of each of the distal gas outlet openings (13 or 13') or the axis of the distal gas tubes can optimally be at an angle range of 10°-35° with respect to the surface of base 19 (see angle D7 shown in FIGS. 5, 6 and 16A) and/or with respect to the plane of the fluid outlets (28 in FIGS. 5, 6 and 16A). In one embodiment of the invention, the oblique position of each of the distal gas outlet openings (13 or 13') is at an angle range of 15°-25° with respect to the level surface of base 19 and/or with respect to the plane of the fluid outlets (28 in FIGS. 5, 6 and 16A).

In one embodiment of the invention, all gas outlet openings in the applicator tip according to the invention are located distal to the outlet openings of the fluid conduits.

In another embodiment of the invention, the distance between the openings of the fluid components positioned at the distal ends of the fluid conduits (e.g. 11, 12) and the center point of the inner diameter of the gas outlet opening is in the range of 0.8-1.2 mm (see distance D4 shown in FIGS. 5, 6 and 16A).

In one embodiment of the invention, the inner diameter of the gas conduit at the distal opening (13 or 13') is 0.4-1.1 mm (see diameter D5 shown in FIGS. 5, 6 and 16A).

The applicator tip according to the invention can be connected to any applicator device and can be used to spray and/or mix the at least two fluids e.g. fibrin sealant component to any surface e.g. a working surface or a surface of a body part of a patient. The surface can be an external surface of the skin that can be seen by unaided vision or a surface of an internal body part which is a part of the internal anatomy of an organism.

The delivery of the fluids to the desired location using the applicator tip can be carried in open surgery or in minimal invasive procedure (MIS) such as by laparoscopy. The term "open surgery" refers to surgery wherein the surgeon gains direct access to the surgical site by a relatively large incision. As used herein the term "minimally invasive procedure" means a surgery wherein the surgeon gains access to the surgical site via small incisions or through a body cavity or anatomical opening e.g. via laparoscopy.

In one embodiment of the invention, the diameter of the entire applicator tip (D10 seen in FIGS. 5, 6 and 16A) ranges from 4.8 to 12 mm e.g. 5 mm or 5.15 mm. In another embodiment of the invention, the applicator tip is inserted to the target area via a trocar in laparoscopic surgery.

In one embodiment of the invention, the applicator tip comprises at least two fluid conduits which extend throughout the tip. In another embodiment of the invention, the fluid conduits are symmetrically arranged with respect to a longitudinal center line of the applicator tip (e.g. line 14 as shown in FIGS. 5, 6 and 16A). In another further embodiment of the invention, the gas conduit of the applicator tip is in gas communication with at least one gas inlet port (6 in FIGS. 2 and 14B). Yet, in another further embodiment of the invention, the gas inlet is in gas connection with two gas outlet openings (13, 13'). In one embodiment of the invention, the two gas outlet openings are positioned directly across from each other. The term "outlet openings" is interchangeable with the term "distal openings".

In another further embodiment of the invention, the gas outlet openings are at an angle range of 10°-35° or at an angle range of 15°-25° with respect to the surface base 19 and/or with respect to the plane where the liquid outlet openings are located (as shown in FIGS. 5, 6 and 16A).

In one embodiment of the invention, the applicator tip comprises: a first port (3); a second port (4); a gas inlet (6); an internal tubing/conduit (7) extending from the first port 3 up to liquid conduit 11; an internal tubing/conduit (8) extending from the second port (4) up to the liquid conduit 12; a gas tubing/conduit (10); a first fluid component outlet opening (22); a second fluid component outlet opening (23); and two opposing gas outlet openings (13, 13').

Figure 15:
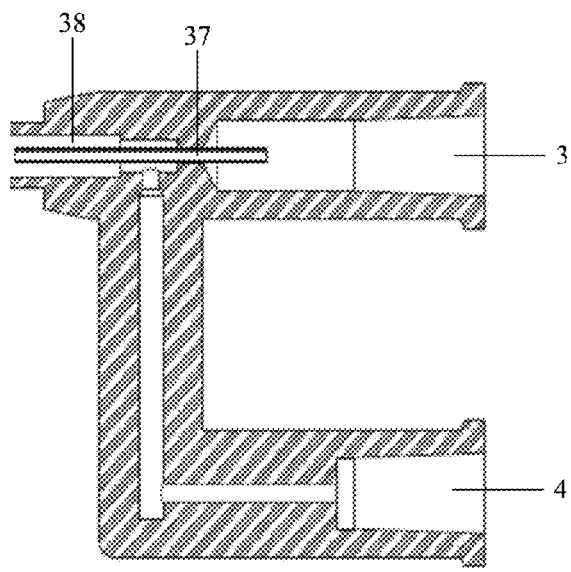
Figure 17A:
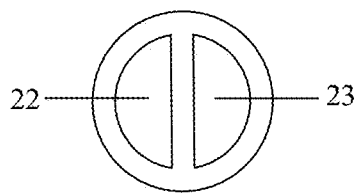
Figure 17B:
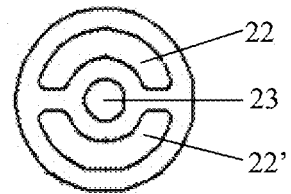

According to some embodiments of the present invention the fluid conduits in the applicator tip are arranged in a concentric double-lumen arrangement comprising an inner lumen (12) and an outer lumen (11) shown in 16A (seen as two lumens 22 and 22' in a frontal view in FIG. 17B surrounding the inner lumen 23). In one embodiment of the invention, port 3 is in fluid communication with the inner lumen 12; and port 4 is in fluid communication with the outer surrounding lumen 11. The connection between the ports and the fluid conduits can be carried out directly or indirectly e.g. port 3 can be connected to lumen 12 via a connecting needle such as a 21G or 23G needle (37 seen in FIG. 15) and port 4 can be connected to lumen 12 through a lumen (38) surrounding needle 37.

In one embodiment of the invention, one component is more viscous than the other. In another embodiment of the invention, the viscous component (e.g. a fibrinogen comprising component) flows in the outer lumen closer to the gas outlet openings when exiting from the fluid opening. In another embodiment, a fibrinogen comprising component flows in the outer lumen and a thrombin comprising component flows in the inner lumen.

In another further embodiment, a thrombin comprising component flows in the outer lumen and a fibrinogen comprising component flows in the inner lumen.

Advantageously, the two reacting components are expelled from the tip and mixing of the components is carried out outside the conduits thereby reducing or preventing clogging of the device with the formed polymer.

The term "mixing" refers to the blending of or contacting of the components.

It was found according to the present invention that using the applicator tip of the invention from a short distance of 2-3 cm from the target area resulted in a thin and smooth texture fibrin layer which homogenously covered the entire sprayed surface. However, spraying with a control applicator tip (which has two parallel fluid conduits with two outlet openings and a gas conduit having one outlet opening—all three openings located on the same plane—as shown in FIG. 7) at such short distance created a thick fibrin layer with irregularities and uncovered regions.

Accordingly, the applicator tip of the invention can be advantageously used when spraying at a distance of less than 10 cm e.g. less than 6 cm from the target surface or tissue for obtaining a thinner and more homogenously fibrin layer which covers the target area, substantially, without leaving regions which are uncovered with the fibrin layer. Thus, the applicator tip of the invention can be advantageously used from a close proximity for effectively controlling bleeding and/or sealing tissues.

It was also found according to the present invention that spraying fibrin sealant components with an applicator tip according to the invention from a distance of 1-2 cm resulted in smaller un-covered area compared to spraying with the control applicator tip from the same distance. Also, it was found that in an application distance of 2-6 cm from the target, using the applicator tip according to the invention resulted in an efficient targeting with full coverage of the target area whereas using the control applicator tip from the same distance resulted in an un-covered diameter of about 1 cm. In view of the homogenous coverage obtained at proximal administration with the tip of the invention, reduced fibrin amounts are sufficient to cover the entire target area thereby economizing in the applied material.

It was also found according to the present invention that spraying with the applicator tip of the invention in short distances from the target (in the range of 1-6 cm) resulted in superior mixing of the components as compared to the control tip when used at the same distance. Accordingly, the applicator tip of the invention can be advantageously used for effectively spraying the fibrin sealant components at a distance of 6 cm or shorter, from the target area while obtaining a substantially full coverage of the target area and superior mixing of the two components.

In one embodiment of the invention, an inlet gas flow rate of 2.8 to 7 L/min or 2.8 to 6 L/min e.g. 4.4 to 6 L/min is used during the spraying of the fibrin sealant components through the applicator tip of the invention.

In another embodiment of the invention, the distance between the distant point of the applicator tip (34) and the target area is less than 6 cm during spraying of the fibrin sealant components.

It was also found according to the present invention that using the applicator tip of the invention in a short distance of 1-6 cm resulted in an efficient targeting even when spraying was carried out using a challenging angle of 90° between the tip and the target area. Oftentimes, spraying under this condition (at an angle of 90°) pushes the fibrin sealant components aside, consequently resulting in formation of un-covered regions as was observed when using the control tip at 90°.

It was found according to the invention that (by a visual inspection) using the applicator tip according to the invention resulted in formation of fine spray i.e. smaller liquid droplets as compared to larger droplets obtained when using the control applicator tip. Typically, small droplets maximize the contact surface area between the two components, enabling superior mixing of the two components and formation of a superior fibrin clot having superior mechanical properties.

It was observed that when spraying a fibrin sealant from a distance of 2-3 cm from the target surface, superior performance was obtained using applicator tips according to the invention having an angle (D7) of the distal gas outlet opening in the range of 15°-25°.

Also, it was found that a gas lumen diameter (D5) of 0.7 and 0.9 mm resulted in the smallest un-covered area and the highest mixing quality when spraying was carried out from a distance of 2-3 cm from the target surface. Thus, it is of advantage to use an applicator tip having a gas outlet opening having a diameter (D5) of higher than 0.4 mm and lower than 1.1 mm for obtaining superior performance e.g. superior targeting and superior mixing efficacy.

It was found that spraying with an applicator tip having a protrusion level of the fluid conduit openings above surface base 19 in the range of 3-3.4 mm resulted in optimal results showing formation of uniform small droplets throughout the administration of 5 ml fibrin sealant. Thus, it is of advantage to use applicator tips having a D4/D8 ratio in the range of 0.235-0.400; or a D8/D11 ratio in the range of 0.71-0.81.

It was found that spraying with an applicator tip according to the invention from a distance of 1-5 cm from the target surface resulted in better mixing of the two components as compared to using the control tip from the same distance. The mixing quality of the tip according to the invention when used from a short distance of 1-5 cm showed similar mixing quality as the control tip when used from its recommended distance from the target (i.e. 10-15 cm from the tip to the tissue surface).

It was found that spraying with an applicator tip according to the invention from a distance of 1-5 cm resulted in better targeting as compared to the control tip (a smaller un-covered diameter was obtained with the tip according to the invention).

Also, it was found that spraying with an applicator tip according to the invention from a distance of 2-5 cm from the target surface resulted in complete coverage of the target surface in a similar manner as the coverage of the control tip when used from its recommended distance from the target (i.e. 10-15 cm from the tip to the tissue surface).

The results show that when spraying from a close proximity to the target area (1-5 cm) the applicator tip according to the invention formed a clot having a diameter similar to the diameter formed when spraying with the control tip from the same short distance and the same fibrin sealant amount. However, the fibrin clot formed with the control tip had un-covered regions or craters.

The results also show that the applicator tip according to the invention achieved a better coverage of the target area than the control tip when spraying was carried out in motion from a close distance.

The results also show that spraying with the applicator tip according to the invention enables beneficial coverage of both small and large target areas when used from a close distance from the surface.

It was found according to the invention that when spraying with the applicator tip according to the invention at a distance of 1-2 cm from the target with the applicator tip according to the invention, an inlet gas pressure of 15-20 psi and a gas flow of equal to 4.5 L/min and up to 6 L/min resulted in optimal mixing.

It was found that when using the applicator tip according to the invention for dripping the two components (i.e. without using a gas), using a concentric fluid lumen arrangement resulted in a shorter migration distance as compared to dripping the components from a side by side fluid arrangement indicating that the concentric arrangement achieved better targeting quality under the tested parameters (see Example 12) as compared to the targeting obtained when using the side by side arrangement. Thus, in order to achieve an efficient targeting when using the tip according to the invention for dripping the liquid components, the fluid conduits can be advantageously arranged concentrically.

Advantageously, it was found that when using the applicator tip according to the invention to spray fibrin sealant in close proximity to a wounded kidney, significantly lower volumes of fibrin sealant needed to stop bleeding as compared to the control tip used at the same short distance.

The Efficacy of the Tip according to the invention was examined in two In-Vivo Models: Rat Kidney Hemorrhage Model and Rabbit Hepatic Wound Model. It was found that using the applicator tip in the Rat Kidney Hemorrhage Model resulted in less blood loss and a higher percentage of non bleeding animals as compared to using the control tip even when using a lower volume of fibrin sealant (both tips were used from a close proximity to the target). It was found that the applicator tip can be beneficially used for stopping bleeding when spraying is carried from a close proximity to the target injured organ. It was observed that using the applicator tip in the Rabbit Hepatic Wound Model effectively prevented adhesion in a similar manner as observed in the control tip (the tip according to the invention was used from a close proximity and the control tip was used according to the instructions for use). No significant difference was found in the rate of fibrin clot degradation when the fibrin was formed using both tips (as observed by the average clot weight at the end of the experiment). In all tested tips no re-bleeding occurred.

Advantageously, optimal results were obtained with an applicator tip comprising the following parameters: distance D1—5 mm; distance D2—1.2 mm; distance D4—0.8 mm; distance D5—0.7 mm; Angle D7—20°; distance D8—3.4 mm; distance D9—1.38 mm; distance D10—5.15 mm; distance D11—4.2 mm; distance D15—2.2 mm; D16—0.100-0.145 mm; ratio D2/D4—1.5; ratio D2/D5—1.71; ratio D4/D8—0.235; ratio D8/D11—0.81; ratio D2/D16—8.3-12.6.

In one embodiment of the invention, one of the fluids comprises thrombin and the other comprises fibrinogen.

The fibrinogen and thrombin can be prepared from initial blood composition. The blood composition can be whole blood or blood fractions, i.e. a product of whole blood such as plasma. Fibrinogen and thrombin can be autologous, human including pooled plasma, or of non-human source. It is also possible that the fibrinogen and the thrombin are prepared by recombinant methods or chemically synthesized.

The thrombin solution can comprise calcium chloride. The concentration of thrombin in the solution can be in the range of from about 2 to about 4,000 IU/ml, or in the range of from about 800 to about 1200 IU/ml. Calcium chloride concentration in the solution can be in the range of from about 2 to about 6.2 mg/ml, or in the range of from about 5.6 to about 6.2 mg/ml, such as in the concentration of 5.88 mg/ml. The thrombin solution may also comprise excipients. As used herein the terms "excipient" refers to an inert substance which is added to the solution. Examples of excipients include, but are not limited to, human albumin, mannitol and sodium acetate. The human albumin in the solution can be in the range of from about 2 to about 8 mg/ml. Mannitol can be in the concentration range of from about 15 to about 25 mg/ml.

Sodium acetate can be added to the solution in the range of from about 2 to about 3 mg/ml.

In one embodiment of the invention, the fibrinogen solution is comprised from a biologically active component (BAC) which is a solution of proteins derived from blood plasma which can further comprise anti fibrinolytic agents such as tranexamic acid and/or stabilizers such as arginine, lysine, their pharmaceutically acceptable salts, or mixtures thereof. BAC can be derived from cryoprecipitate, in particular concentrated cryoprecipitate.

The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitate supernatant that contains fibrinogen and factor XIII. The precipitate can be collected, for example by centrifugation and dissolved in a suitable buffer such as a buffer containing 120 mM sodium chloride, 10 mM trisodium citrate, 120 mM glycine, 95 mM arginine hydrochloride, 1 mM calcium chloride. The solution of BAC can comprise additional factors such as for example factor VIII, fibronectin, von Willebrand factor (vWF), vitronectin, etc. for example as described in U.S. Pat. No. 6,121,232 and WO9833533. The composition of BAC can comprise stabilizers such as tranexamic acid and arginine hydrochloride. The amount of tranexamic acid in the solution of BAC can be from about 80 to about 110 mg/ml. The amount of arginine hydrochloride can be from about 15 to about 25 mg/ml.

Optionally, the solution is buffered to a physiological compatible pH value. The buffer can be composed of glycine, sodium citrate, sodium chloride, calcium chloride and water for injection as a vehicle. Glycine can be present in the composition in the amount of from about 6 to about 10 mg/ml, the sodium citrate can be in the range of from about 1 to about 5 mg/ml, sodium chloride can be in the range of from about 5 to about 9 mg/ml and calcium chloride can be in the concentration of about 0.1-0.2 mg/ml.

In another embodiment, the concentration of plasminogen and plasmin in the BAC composition is lowered to equal or less than 15 µg/ml like for example 5 µg/ml or less plasminogen using a method as described in U.S. Pat. No. 7,125,569, EP 1,390,485 and WO02095019. In another embodiment of the invention, when the concentration of plasminogen and plasmin in the BAC composition is lowered, the composition does not contain tranexamic acid.

The disclosure of applications, patents and publications, cited above or below, is hereby incorporated by reference.

EXAMPLES

Fibrinogen and Thrombin Components

The fibrinogen component used in the experiments described below is the Biological Active Component 2 (BAC2) of EVICEL® fibrin sealant (Omrix Biopharmaceuticals Ltd.), and the thrombin component used is as the thrombin component of EVICEL® fibrin sealant (Omrix Biopharmaceuticals Ltd.).

Example 1

Applicator Tip Structure

Two different applicator tips (9) having two parallel fluid conduits with two outlet openings, and a gas tube having two opposing outlet openings located distal to the two outlet openings of the fluid conduits were assembled—see FIGS. 5 and 6. The applicator tip shown in FIG. 6 had the following specific parameters: distance D1 which is the vertical distance from the base plate (19) to a distant point of the tip (34)—4 mm; distance D2 which is the vertical distance from a center line of the tip (14) to the gas opening (13, 13')—1.2 mm; distance D4 which is the vertical distance from plane 28, where the outlet openings are positioned, to a center point of the gas opening—1.1 mm; distance D5—the diameter of the gas opening—0.7 mm; angle D7 which is the angle of the distal gas tube (25) with respect to plane (28) and/or with respect to base plate 19—20°; Distance D8 which is the distance from the base plate (19) to plane 28 where the outlet openings are positioned—2.7 mm.

The applicator tip shown in FIG. 5 had the same parameters only that: distance D1 was 1.4 mm; distance D6 (the diameter of the proximal gas tube) was 0.5 mm; and the fluid conduits did not protrude above surface level 19 (distance D8=0 mm).

The above specified applicator tips were used in Examples 2-5 below.

Example 2

Performance Characteristics of the Applicator Tip

In order to effectively control bleeding and/or seal tissues, the injured area must be homogenously covered with a fibrin sealant layer. The following experiment was aimed to examine whether an applicator tip according to the invention enables to homogenously cover a surface with a fibrin layer by spraying the fibrin sealant components [fibrinogen (BAC2) and thrombin] from a short distance to the surface of 3-4 cm.

For this purpose, the fibrin sealant components were sprayed onto a 4×5 cm (20 cm$^2$) surface area at a gas flow rate of 6 L/min (an inlet gas pressure of 20 psi was used) using the applicator tip described in Example 1 and shown in FIG. 5.

An applicator tip having two parallel fluid conduits with two outlet openings, and a gas conduit having one outlet opening, all three openings located on the same surface was used as reference/control (a frontal view of the control applicator tip showing the location of the three openings is shown in FIG. 7). According to the instruction for use in the EVICEL® kit, when using the device for spraying, the recommended spray pressure is 20-25 psi at a distance of 10-15 cm from the end of the applicator tip to the tissue surface.

In all the described experiments, for spraying the fibrin sealant components, each of the two applicator tips (control and the tip according to the invention) were connected to an applicator device as described in WO2007059801 wherein the applicator tip according to the invention is at the end of a manifold structure. The connection was carried out through a fluid control device as described in WO9810703 (a drawing of the applicator tip (9) according to one embodiment of the invention connected to the applicator device (2) is shown in FIG. 1).

EVICEL® Fibrin Sealant (manufactured by OMRIX Biopharmaceuticals LTD.) was used in this experiment (using an equal volume of thrombin component and BAC2 component in a total volume of 5 ml).

Both applications (using the applicator tip according to the invention or the control tip) were carried out at a short distance of 3-4 cm from the 20 cm$^2$ surface (i.e. the control tip was not used at the recommended distance). The spraying was carried out crosswise at an angle of 50° with respect to the surface.

Figure 8A:
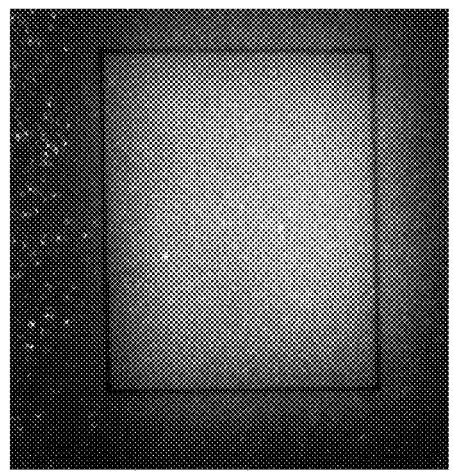

Following clot formation (about 1 minute), the sprayed surface was photographed. FIGS. 8A and B show black and white pictures of the sprayed surface when using the applicator tip according to the invention and the control applicator tip, respectively.

Figure 8B:
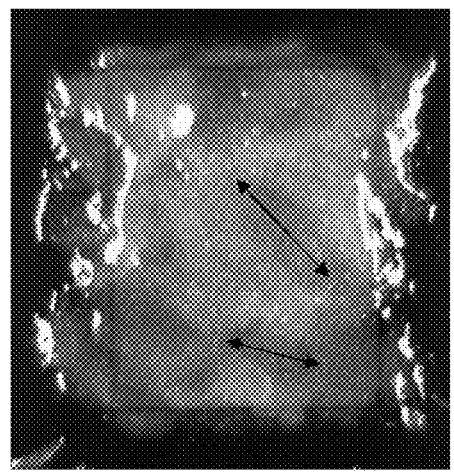

It was observed that spraying at a short distance of 3-4 cm using the applicator tip according to the invention resulted in a thin and smooth texture fibrin layer which homogenously covered the entire sprayed surface (FIG. 8A). However, spraying with the control tip (which is typically used at a distance of 10-15 from the target) created a thick fibrin layer with irregularities and uncovered regions (FIG. 8B). The arrows in FIG. 8B mark the localization of the uncovered regions.

In another set of experiments, the targeting quality of the applicator tip shown in FIG. 5 was evaluated by assessing the ability of the applicator tip to target the middle point of an "X" shaped mark.

For this purpose, an "X" shaped mark was drawn, and fibrin sealant (EVICEL®) was sprayed from various distances (in the range of 1-6 cm from the middle point of the "X" mark) using the applicator tip according to FIG. 5 or using the control tip. The spraying was carried out at an angle of 90° with respect to the mark, and at a gas flow rate of 6 L/min. An equal volume of thrombin component and BAC2 component were used in a total volume of 1 ml.

Figure 9:
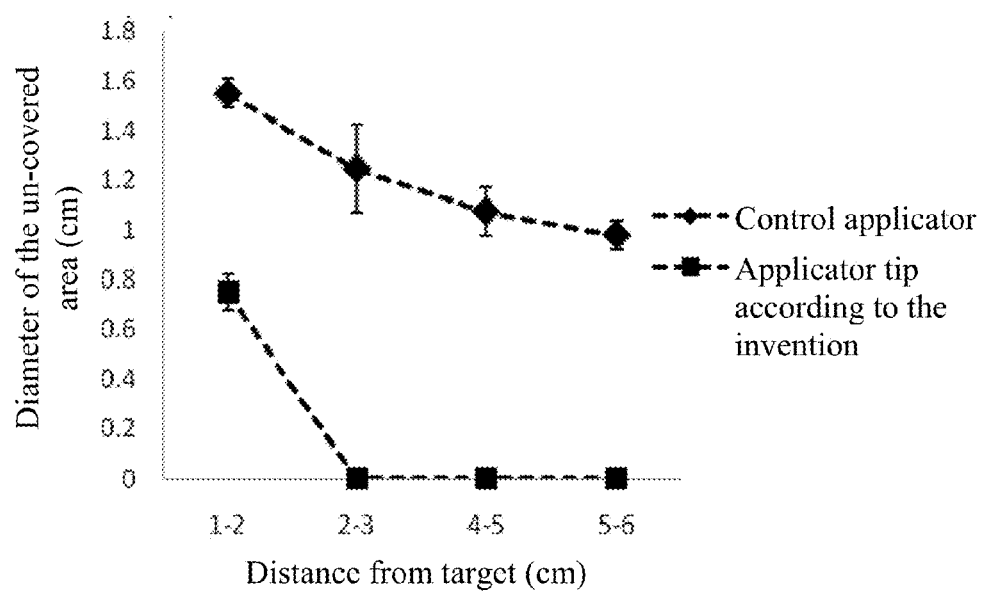

Following clot formation (about 1 minute), the sprayed "X" mark was photographed and the efficacy of targeting the middle point of the mark was examined by measuring the diameter of the un-covered area. A graph plotting the spraying distance from the middle point of the "X" mark against the diameter of the un-covered area is shown in FIG. 9.

Figure 10A:
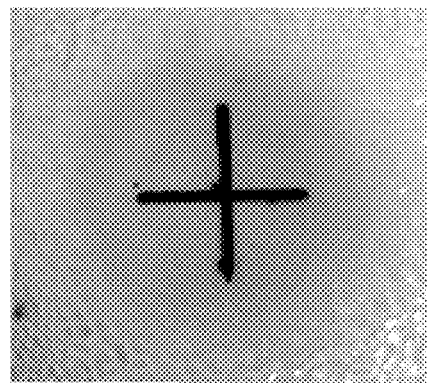

FIGS. 10A and B show representative pictures of an experiment carried out in a similar manner to the above described experiment (A—spraying with the applicator tip according to FIG. 5; B—spraying with the control applicator tip) wherein spraying was carried out at a distance of 3-4 cm from the target ("X" mark). The arrow in FIG. 10B shows the diameter of the uncovered area.

It was observed (FIG. 9) that spraying with an applicator tip according to FIG. 5 (applicator tip according to the invention) from a distance of 1-2 cm resulted in a shorter diameter of an un-covered area as compared to the diameter of an un-covered area obtained when spraying with the control applicator tip. Also, it was observed (FIGS. 9 and 10A and B) that in an application distance of 2-6 cm from the target, using the applicator tip according to FIG. 5 resulted in an efficient targeting, since the middle point of the mark was entirely covered, whereas using the control applicator tip resulted in an un-covered diameter of about 1-1.2 cm.

As shown in the previous experiment, FIGS. 10A and B also show that using the applicator tip according to FIG. 5 resulted in a thinner, and more homogenously applied fibrin layer which advantageously covered the target area without leaving regions which are uncovered with a fibrin layer.

Figure 10B:
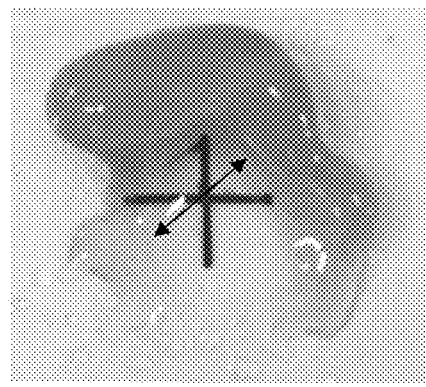

It was also observed that using the applicator tip of the invention in a short distance of 2-6 cm resulted in an efficient targeting even when the spraying was carried out at a challenging angle of 90° with respect to the target area (an angle which may result in pushing of the biological fluids aside by the gas flow consequently resulting in formation of un-covered regions or craters—as observed when using the control tip—FIG. 10B).

These results indicate that using the applicator tip according to the invention enables better targeting quality as compared to the control tip with full and homogeneous coverage of the target area when applied at distances of 2-6 cm from the target surface.

In another experiment, the mixing quality of the applicator tip according to the invention was evaluated. The evaluation was carried out by spraying a thrombin component which was supplemented with blue dye (10% v/v) and a BAC2 component which was supplemented with yellow dye (10% v/v) (0.4 ml total volume).

The spraying was carried out from various distances from the target surface (in the range of 1-6 cm) using the applicator tip according to the invention and shown in FIG. 6 or the control tip in a similar manner as described above. The spraying was carried out at an angle of 90° with respect to the surface, and at a gas flow rate of 6 L/min (an inlet gas pressure of 20 psi was used).

Following spraying, the color of the obtained clot was assessed by a visual inspection according to the following ranking scale: 1—no mixing—blue and yellow colors were obtained; 2—three colors were obtained: mostly blue and yellow with a low level of green; 3—three colors were obtained: mostly green with a low level of un-mixed blue and yellow; 4—three colors were obtained: mostly green with a low level of one of the un-mixed colors—blue or yellow; 5—complete mixing/efficient mixing—a fully mixed green color was obtained.

Table 1 shows the mixing quality (using the 1-to-5 ranking scale) from the various distances when using the applicator tip according to the invention and the control tip.

TABLE 1

The quality mixing of the applicator tip according to the invention.

| Distance from | Mixing rank (1-to-5) | |
|---|---|---|
| surface (cm) | Applicator tip according to the invention | Control applicator tip |
| 1 | 4 | 3 |
| 2-3 | 5 | 3 |
| 4-5 | 5 | 3 |
| 5-6 | 4.5 | 3 |

It was observed that using the applicator tip of the invention resulted in superior mixing of the two components as compared to the mixing obtained by the control tip when spraying at close proximity to a surface (a distance of 1-6 cm from the distance).

A visual inspection of the obtained liquid droplets following atomization (i.e. encounter of the liquid components with the gas) revealed that using the applicator tip according to the invention resulted in formation of fine spray i.e. smaller liquid droplets as compared to the droplets obtained when using the control applicator tip.

Example 3

Effect of the Angle of the Distal Gas Outlet Openings (Angle D7) on the Applicator Tip Performance In the following Example, the targeting quality of the applicator tip was evaluated. The applicator tip evaluated in this experiment had a similar geometric structure as the applicator tip described in FIG. 5 except for angle D7, which establishes the oblique position of each of the distal gas outlet openings, which was 35° (instead of an angle of 20° as in the tip of FIG. 5). In this experiment, the targeting quality was assessed by the ability of the applicator tip to target the middle point of a surface when spraying from close proximity.

In this experiment, the spraying was carried out from two distances from the middle point of the target surface-1-2 cm or 2-3 cm; the spraying angle between the tip and the target surface was 90°; an equal volume of thrombin component and BAC2 component were used in a total volume of 0.4 ml; and the application was carried out at an inlet gas pressure of 20 psi, and a gas flow rate of 6 L/min.

The performance of an applicator tip having a D7 angle of 35° was compared to that of the applicator tip of FIG. 5 having a D7 angle of 20° and of the control tip.

Figure 11:
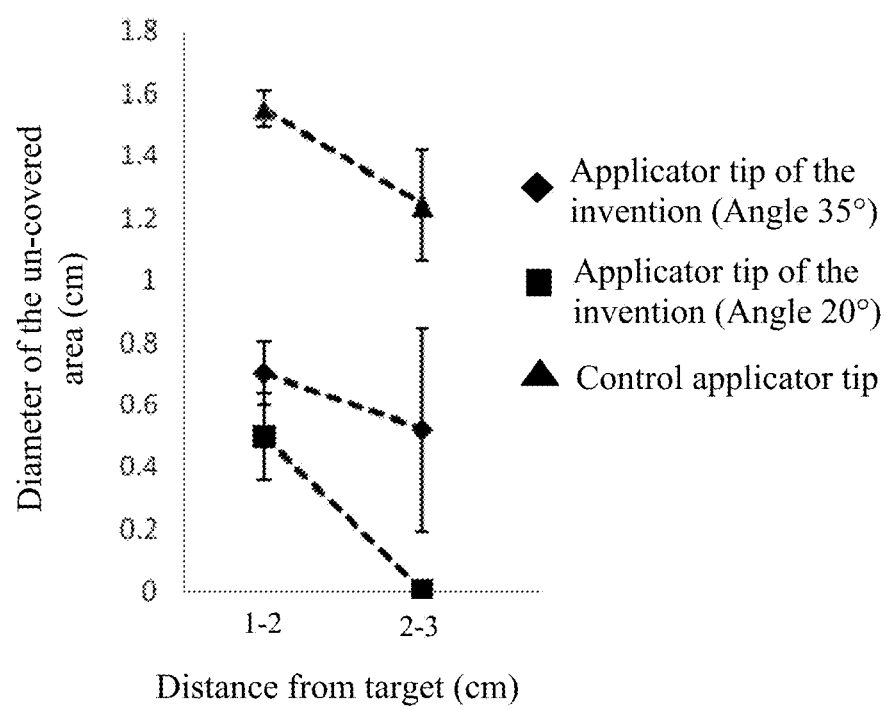
Figure 12A:
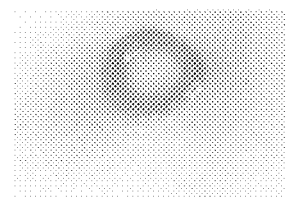
Figure 12B:
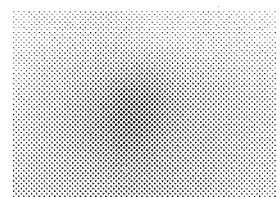
Figure 12C:
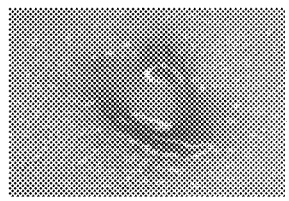
Figure 12D:
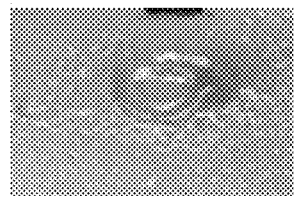
Figure 12E:
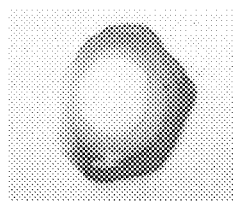
Figure 12F:
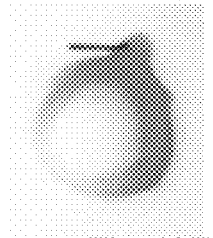
Figure 13:
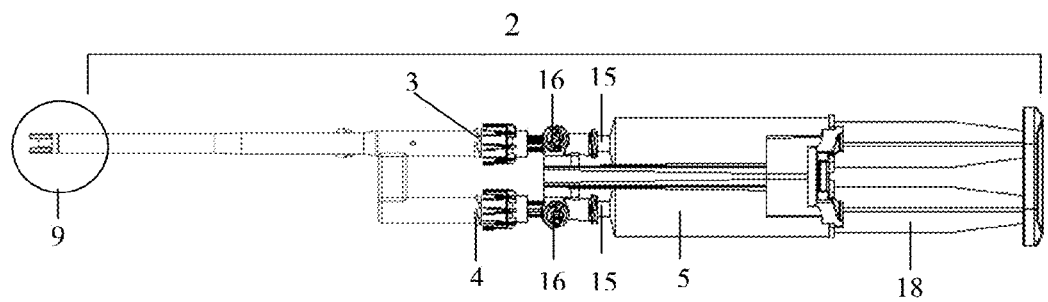

Following clot formation (about 1 minute), the sprayed surface was photographed and the targeting quality was examined by measuring the diameter of the un-covered area. A graph plotting the spraying distance from the middle point of the surface against the diameter of the un-covered area is shown in FIG. 11.

FIGS. 12A-F show representative pictures of the formed clots using the different applicator tips and under the different spraying distances: FIGS. A, B correspond to spraying with a tip shown in FIG. 5 having D7 angle of 20°. FIGS. C, D correspond to spraying with a tip shown in FIG. 5 having an increased D7 angle of 35°. FIGS. E, F correspond to spraying with a control tip having no D7 angle. FIGS. B, D and F correspond to spraying from a distance of 2-3 cm and FIGS. A, C, and E correspond to spraying from a shorter distance of 1-2 cm. The arrows in the Figs. show the diameter of the uncovered area.

It was observed (FIG. 11) that spraying from a distance of 1-2 cm with both tips having a D7 angle of 20° and 35° resulted in better area coverage as compared to the area coverage obtained when spraying with the control applicator tip. Also, it was observed that the applicator tips with 20° and 35° angles showed superior targeting quality as compared to the control tip. The results show also that D7 of 20° was superior to D7 of 35°. Optimal results (complete coverage of the middle point) were achieved with the applicator tip having a D7 angle of 20° and used at the distance of 2-3 cm.

The effect of the angle of the distal gas outlet opening (D7 angle) on the performance of the tip was evaluated in another experiment. The evaluation was carried out by examining the targeting and mixing quality of the tip.

The applicator tips evaluated in this experiment had a similar geometric structure as the tip shown in FIG. 6 except that: 1—the angle of the gas lumen (angle D7) was 15°, 20°, 25° or 35°; and 2—two different fluid conduit arrangements were used: one—having the two component fluid conduits arranged side by side (two parallel fluid conduits so that the BAC2 component conduit is side by side with the thrombin component conduit as shown in FIGS. 6 and 17A), and another—having the two component fluid conduits arranged concentrically so that the thrombin was fed in the inner lumen and the BAC2 was fed in the outer lumen (as shown in FIG. 17B).

An angle of 15° and 20° was examined with the concentric arrangement type, and an angle of 25° and 35° was examined with the side by side arrangement. Of note, it was found that under the examined parameters (e.g. application by spraying), the fluid conduit arrangement had similar performance in the targeting and mixing quality (data not shown).

The different parameters (targeting and mixing quality) were evaluated by spraying the fibrin sealant components towards a horizontal surface. The spraying was carried out from a distance of 2-3 cm from the target surface; the inlet gas pressure was set to 15 psi; the spraying angle between the tip and the target surface was 90°; and an equal volume of thrombin component and BAC2 component were used in a total volume of 0.4 ml.

Following clot formation, both the targeting quality (by measuring the diameter of the un-covered area) and the mixing quality (by a visual inspection of the color of the obtained clot according to the ranking scale described above) were evaluated. The results are shown in Table 2 below.

TABLE 2

The targeting and mixing quality of an applicator tip in different angles of the distal gas outlet opening.

| Tested Parameter | Gas Outlet Opening Angle | | | |
|---|---|---|---|---|
| | 15° | 20° | 25° | 35° |
| Diameter of the un-covered area (cm) | 0.0 ± 0.0 (A) | 0.08 ± 0.21 (A) | 0.0 ± 0.0 (A) | 0.05 ± 0.14 (A) |
| Mixing Quality (1-to-5) | 5.0 ± 0.0 (A) | 4.84 ± 0.35 (A) | 5.0 ± 0.0 (A) | 4.0 ± 0.0 (B) |

\* N (number of replicates) = 4, 16, 2, 2 for a D7 angle of 15°; 20°; 25°; and 35°, respectively.
\*\* ANOVA tests were carried out for each tested parameter separately. No statistical significance was found in the "Diameter of the un-covered area". In the "Mixing Quality", statistical significance between groups A and B is p < 0.01.

With regards to the targeting quality, it was observed that in all tested angles (15°-35°, under the tested parameters, spraying resulted almost in complete coverage of the surface (see the value of the diameter of the un-covered area).

With regards to the mixing quality, it was observed that superior mixing was obtained with an applicator tip having a D7 angle in the range of 15°-25°. These results are concordant with the previous results showing that an applicator tip having a D7 angle of 20° is superior to an applicator tip having a D7 angle of 35°.

Taking into consideration all the parameters tested in these experiments (targeting and mixing quality), it was found that the optimal angle of the distal gas outlet opening in the tip is in the range of 15°-25°.

Example 4

Effect of the Distal Gas Outlet Openings Diameter (D5) on the Applicator Tip Performance In the following example, the targeting and mixing quality of the applicator tip was evaluated in different tips comprising a distal gas outlet opening (D5) of different diameters.

The applicator tips used in this experiment had a similar geometric structure as shown in FIGS. 6 and 17A with the side by side fluid arrangement or had a similar geometric structure as in the tip in FIGS. 13, 14, 15, 16 and 17B with the concentric fluid arrangement. The following gas lumen outlet diameters (D5) were tested: 0.4, 0.7, 0.9, or 1.1 mm. The side by side tip tested had D5 diameters of 0.4, 0.9, and 1.1 mm. The concentric tip tested had a D5 diameter of 0.7 mm. As indicated above, when spraying, targeting and mixing qualities were found to be similar in tips having concentric or side by side fluid arrangements.

The spraying conditions such as the distance from target surface, spraying angle, inlet gas pressure, and volumes of thrombin and BAC2 components were the same as in the previous experiment. Spraying was carried out towards a horizontal plane as above.

Both evaluations were carried out following clot formation: targeting by measuring the diameter of the un-covered area; and mixing quality by a visual inspection of the color of the obtained clot according to the scale described above.

The obtained results are shown in Table 3 below.

TABLE 3

The targeting and mixing quality of an applicator tip having different diameters of the distal gas outlet opening.

| Tested Parameter | Distal Gas Outlet Opening Diameter (mm) | | | |
|---|---|---|---|---|
| | 0.4 | 0.7 | 0.9 | 1.1 |
| Diameter of the un-covered area (cm) | 1.4 ± 0.14 (A) | 0.08 ± 0.21 (B) | 0.00 ± 0.00 (B) | 0.9 ± 0.14 (A) |
| Mixing Quality (1-to-5) | 3.0 ± 0.0 (A) | 4.84 ± 0.35 (C) | 4.50 ± 0.71 (B, C) | 3.5 ± 0.71 (A, B) |

\* N (number of replicates) = 2, 16, 2, 2 for a D5 value of 0.4, 0.7, 0.9, and 1.1 mm, respectively.
\*\* ANOVA tests were carried out for each tested parameter separately. Statistical siginificance in "Diameter of the un-covered area" between groups A and B is p < 0.01. Statistical siginificance in "Mixing Quality" between groups A, B and C is p < 0.01.

It was observed that a gas lumen diameter of 0.7 and 0.9 mm resulted in the smallest un-covered area and the highest mixing quality.

Thus, it is of advantage to use an applicator tip having a distal gas outlet opening diameter of higher than 0.4 mm and lower than 1.1 mm for obtaining superior performance e.g. superior targeting and superior mixing efficacy.

Example 5

Effect of the Distance (D8) of the Fluid Conduit Openings from a Surface Base (19) on the Droplet's Size in the Formed Spray Generally, small droplets enable superior mixing of the fibrin sealant components as compared to the mixing of the fibrin sealant components when formed from larger droplets.

In the following experiment, the size of droplets in the spray formed using applicator tips having fluid conduit openings located at different distances (or protrusion levels, D8 in FIG. 6) from the surface base (19 in FIG. 6) were tested. Protrusion levels in the range of 2.4 to 4.2 mm above surface level/base 19 (as shown in FIG. 6) were tested. The rest of the geometric structure was as described in Example 1 for the tip shown in FIG. 6.

In this experiment, 2.5 ml BAC2 and 2.5 ml thrombin components were sprayed in 400 μl portions (with about 1-2 seconds interval between each portion sprayed), and the volume administered until the spray pattern has changed from a homogenous spray of uniform small droplets to a heterogeneous spray of small and large droplets was monitored. The change in uniformity is due to accumulation of fibrin clot on the fluids and/or gas outlet openings. The size of the droplets was visually inspected.

In this experiment, spraying was carried out at an inlet gas pressure set to 15 psi.

Figures 18, 19:
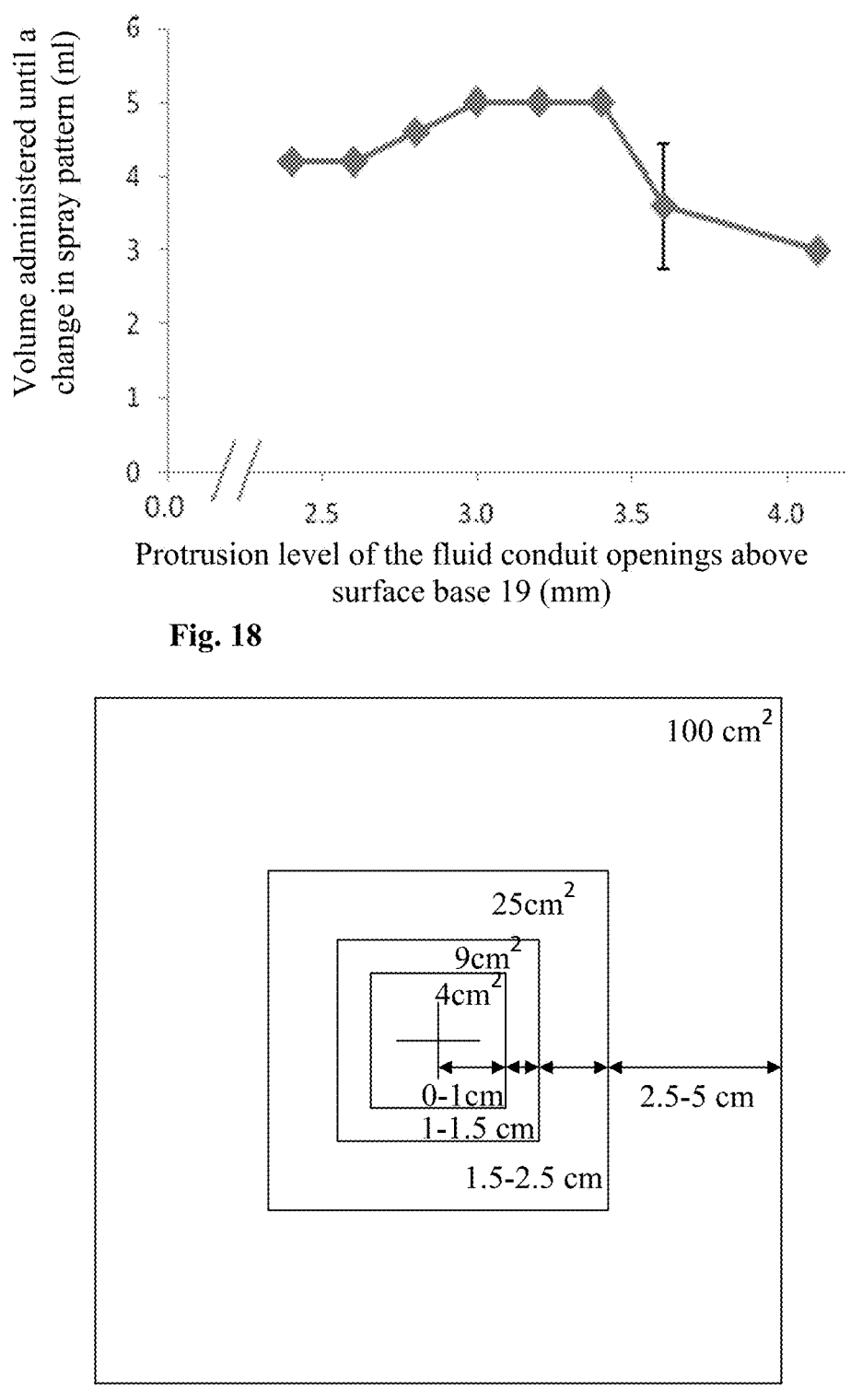

A graph plotting the protrusion level of the fluid conduits opening above surface base 19 against the volume administered until a change in the spray pattern was observed is shown in FIG. 18.

In the beginning of the spraying procedure a homogenous spray of uniform small droplets was obtained in all tested tips with different protrusion levels. It was found that spraying with an applicator tip having a protrusion level in the range of 3-3.4 mm above the level of surface base 19 resulted in optimal results showing formation of uniform small droplets throughout the administration of 5 ml.

Thus, it is of advantage to use tips having D4/D8 ratios between 0.235 and 0.400 or having D8/(D4+D8) ratio between 0.71 and 0.81.

Example 6

The Performance of an Optimal Applicator Tip According to the Invention

In the following set of experiments, the performance of an applicator tip having a concentric fluid conduit arrangement and a D7 angle, D5 and D8 distances within the optimal ranges was examined.

The following are the specific parameters of the tip as shown in FIG. 16A: distance D1 which is the vertical distance from the base plate (19) to a distant point of the tip (34)—5 mm; distance D2—which is the vertical distance from a center line of the tip (14) to the gas opening (13, 13')—1.2 mm; distance D4—which is the vertical distance from plane 28, where the outlet openings are positioned, to a center point of the gas opening—0.8-1.2 mm; diameter D5—the diameter of the gas opening=diameter D6 (the diameter of the proximal gas tube)—0.7 mm; angle D7—which is the angle of the distal gas tube (25) with respect to plane (28) and/or with respect to base plate (19)—20°; distance D8—which is the distance from the base plate (19) to plane 28 where the outlet openings are positioned—3-3.4 mm; distance D9 is the distance from the plane where the gas opening (13) is positioned to the outer wall of the structure that encapsulates the gas conduit (33a and b)—1.38 mm; distance D10 which is the overall diameter of the tip—5.15 mm; distance D11 which is the vertical distance from the base plate (19) to a center point of the gas outlet opening—4.2 mm; distance D15 is the width of the structure (33a and 33b) that encapsulates the gas conduit—2.2 mm.

The performance of the applicator tip according to the invention for use in close proximity to a surface was compared to the performance of the control tip described above.

In all the experiment carried out with the concentric fluid arrangement, the thrombin was fed in the inner lumen and the BAC2 was fed in the outer lumen and therefore the BAC2 viscous liquid component is closer to the gas outlet openings than the non viscous thrombin liquid component when exiting from the fluid opening.

I—Evaluation of the Mixing Quality

The mixing quality was visually evaluated according to the 1-to-5 ranking scale described above by spraying 0.4 ml dyed thrombin and BAC2 components (at equal volumes) from various distances in the range of 1-5 cm from a horizontal target surface and evaluating the color of the obtained fibrin clot. The inlet gas pressure used was 15 psi for the applicator tip according to the invention, and 25 psi for the control tip; the spraying angle between the device and the target surface was 90° in both tips.

As indicated above, the recommended spray pressure for the control tip is 20-25 psi, and the distance is 10-15 cm from the tip to the tissue surface.

The results are shown in Table 4 below.

TABLE 4

The mixing quality of an applicator tip according to the invention.

| | Distance from target (cm) Mixing Rank (1-to-5) | | |
|---|---|---|---|
| Applicator tip | 1-2 | 2-3 | 4-5 |
| Control applicator tip* | 4.13 ± 0.35 | 3.17 ± 1.03 | 3.50 ± 0.89 |
| Applicator tip according to the invention** | 4.72 ± 0.45 | 4.84 ± 0.35 | 5.00 ± 0.00 |

\*N = 8, 12, and 8 replicates for 1-2, 2-3, and 4-5 cm distance from target, respectively.
\*\*N = 16, 16 and 4 replicates for 1-2, 2-3, and 4-5 cm distance from target, respectively.
\*\*\*Statistical analysis (TTEST) was carried out between the two tested tips for each distance from the target and the results were found to be significant (p < 0.01).

It was observed that spraying with an applicator tip according to the invention from a distance of 1-5 cm from the target resulted in better mixing of the two components as compared to using the control tip from the same distance.

The mixing quality of the tip according to the invention when used from a short distance of 1-5 cm showed similar mixing quality as the control tip when used from its recommended distance from the target (data not shown).

II—Evaluation of the Targeting Quality

In another set of experiments, the targeting quality of the above described applicator tip was evaluated. The evaluation was carried out by assessing the ability of the applicator tip to target the middle point of a surface with a fibrin layer. The spraying of the two components was carried out towards a horizontal surface using the conditions and volumes described in the previous mixing quality assessment (see point I above).

Following clot formation, the targeting quality was assessed by measuring the diameter of the un-covered area. To evaluate the coverage area obtained by both tips, the diameter of the formed clot was measured.

The results are shown in Table 5 and 6 below.

TABLE 5

The targeting quality of an applicator tip according to the invention.

| | Distance from target (cm) Uncovered area diameter (cm) | | |
|---|---|---|---|
| Applicator tip | 1-2 | 2-3 | 4-5 |
| Control applicator tip* | 1.28 ± 0.30 | 1.25 ± 0.16 | 1.05 ± 0.08 |
| Applicator tip according to the invention** | 0.81 ± 0.31 | 0.08 ± 0.21 | 0.00 ± 0.00 |

*N = 8, 12, and 8 replicates for 1-2, 2-3, and 4-5 cm distance from the target, respectively.
**N = 16, 16 and 4 replicates for 1-2, 2-3, and 4-5 cm distance from target, respectively.
***Statistical analysis (TTEST) was carried out between the two tested tips for each distance from the target and the results were found to be significant (p < 0.01).

TABLE 6

The clot size obtained following spraying with the applicator tip according to the invention and with the control tip.

| | Distance from target (cm) Clot size Diameter (cm) | | |
|---|---|---|---|
| Applicator tip | 1-2 | 2-3 | 4-5 |
| Control applicator tip* | 2.89 ± 0.33 | 3.11 ± 0.60 | 3.08 ± 0.49 |
| Applicator tip according to the invention** | 3.02 ± 0.39 | 3.11 ± 0.39 | 2.90 ± 0.18 |

*N = 8, 12, and 8 replicates for 1-2, 2-3, and 4-5 cm distance from the target, respectively.
**N = 16, 16 and 4 replicates for 1-2, 2-3, and 4-5 cm distance from target, respectively.
***Statistical analysis (TTEST) was carried out between the two tested tips for each distance from the target and no significant difference was found.

It was observed that spraying with an applicator tip according to the invention from a distance of 1-5 cm resulted in better targeting as compared to the control tip (a smaller un-covered diameter was obtained with the tip according to the invention).

Also, it can be seen that spratying with an applicator tip according to the invention from a distance of 2-5 cm from the target resulted in complete coverage of the target surface in a similar manner as the coverage of the control tip when used from its recommended distance from the target (data not shown).

Table 6 shows that at all tested spraying distances, using both applicator tips resulted in a clot having a similar diameter. The obtained diameters were also similar to the results of the control when used from its recommended distance from the target (data not shown).

Example 7

Targeting Quality of the Applicator Tip—Spraying with an Amplitude Movement

In the above experiments it was shown that the applicator tip according to the invention can be effectively used to create a thin fibrin layer with a homogenous and full coverage of the sprayed area when spraying is carried out from one point with no motion. However, typically in surgery spraying is carried out by moving the tip back and forth over the target surface. Thus, in the following experiment, the targeting quality of the tip was examined following spraying in motion.

The targeting quality of the tip described in Example 6 (FIG. 16) was compared to that of the control tip.

Spraying was carried out towards a marked point from a distance of 1-2 cm or from a distance of 2-3 cm; the inlet gas pressure was set to 15 psi or 20 psi (when using the applicator tip according to the invention) or 25 psi (when using the control applicator tip); the angle between the tip and the target surface was 90°; an equal volume of thrombin component and BAC2 component were used in a total volume of 0.4 ml.

Spraying was carried out while moving the tip 1 cm to each sided of the middle point of the mark i.e. a movement amplitude of 2 cm. Following clotting of the two components, the diameter of the uncovered area was measured. The results are shown in Table 7 below.

TABLE 7

Targeting quality of the applicator tip when spraying is carried out in motion.

| | | Diameter of the uncovered area (cm)* | |
|---|---|---|---|
| | Pressure (psi) | Distance from target 1-2 cm | Distance from target 2-3 cm |
| Control tip** | 25 | 0.97 ± 0.15 (A) | 0.87 ± 0.06 (A) |
| Applicator tip according to the invention*** | 20 | 0.45 ± 0.07 (B) | 0.00 ± 0.00 (C) |
| | 15 | 0.00 ± 0.00 (C) | 0.00 ± 0.00 (C) |

*ANOVA tests were carried out for each tested distance (1-2 cm or 2-3 cm) separately. p < 0.01.
**N = 3 replicates for each distance.
***N for 20 psi = 2 replicates for each distance; N for 15 psi = 4, 2 replicates for 1-2 and 2-3 cm, respectively.

In general, the results show that the applicator tip according to the invention achieved a better coverage than the control tip when spraying is carried out in motion from a close distance.

Specifically, it was observed that sparying during movement with the applicaor tip according to the invention at 15 psi resulted in full coverage of the sprayed area at all tested distances. Of note, spraying from one point with the applicator tip according to the invention at the same conditions (15 psi) resulted in an un-covered diameter of 0.81±0.31 and 0.08±0.21 cm for 1-2 and 2-3 cm, respectively (see Table 5).

Also, it was observed that spraying with the applicator tip according to the invention at 20 psi during movement resulted in full coverage of the sprayed area at a distance of 2-3 cm from the target.

Example 8

Fibrin Dispersion Pattern Around a Target Location following Spraying with the Applicator Tip In the following example, the dispersion pattern of a sprayed fibrin sealant around a focal/center point was examined when using the applicator tip according to the invention (as shown in FIG. 16). The spray dispersion pattern of the applicator tip according to the invention was compared with that of the control tip.

An efficient coverage can be obtained when a sprayed liquid is dispersed evenly or un-evenly around a focal point e.g. the sprayed material can homogenously cover a large area or alternatively, most of the sprayed material can accumulate at a center point. Generally, an even distribution is useful to cover a large target whereas an un-even distribution having the majority of the material at the focal point can be useful when the user wishes to cover a small target.

For this purpose, four transparent square sheets having an area of 100, 25, 9, and 4 $cm^2$ were piled with the 4 $cm^2$ sheet being on top (FIG. 19). The sheets were aligned according to the center point of each sheet. Following the alignment, the exposed distance of the x-axis from the focal point of all the sheets was measured and found to be 0-1 cm, 1-1.5 cm, 1.5-2.5 cm, and 2.5-5 cm for the 4, 9, 25, and 100 $cm^2$ sheets, respectively (see the black arrow on each illustrated sheet in FIG. 19). Before piling the sheets on each other, the weight of each sheet (the empty sheet) was measured.

In the next step, 1 ml BAC2 and 1 ml thrombin were sprayed towards the center point of the sheets, and following clot formation the clot was cut according to the outer line of each sheet. The weight of each sheet was measured and the net clot weight on each sheet was calculated by subtracting the weight of the empty sheet prior to spraying.

In order to calculate the distribution of the fibrin around the center point, the clot percentage sprayed on each sheet was calculated by dividing the obtained net clot weight into the total clot weight (obtained by mixing 1 ml BAC2 and 1 ml thrombin using a pipette—considered as 100%).

In this experiment, the applicator tip was used from a short distance of 1-2 or 5 cm from the center point at a pressure of 15-20 psi; and the control tip was used from a distance of 10 or 15 cm from the center point at a pressure of 25 psi (according to the manufacturer recommendation). The application angle between the tip and the target was 90°. For applicator tip according to the invention—N=19 and 8 for a distance of 1-2 and 5 cm from the target, respectively. For control tip—N=9 and 3 for a distance of 10 and 15 cm from the target, respectively.

Figure 20:
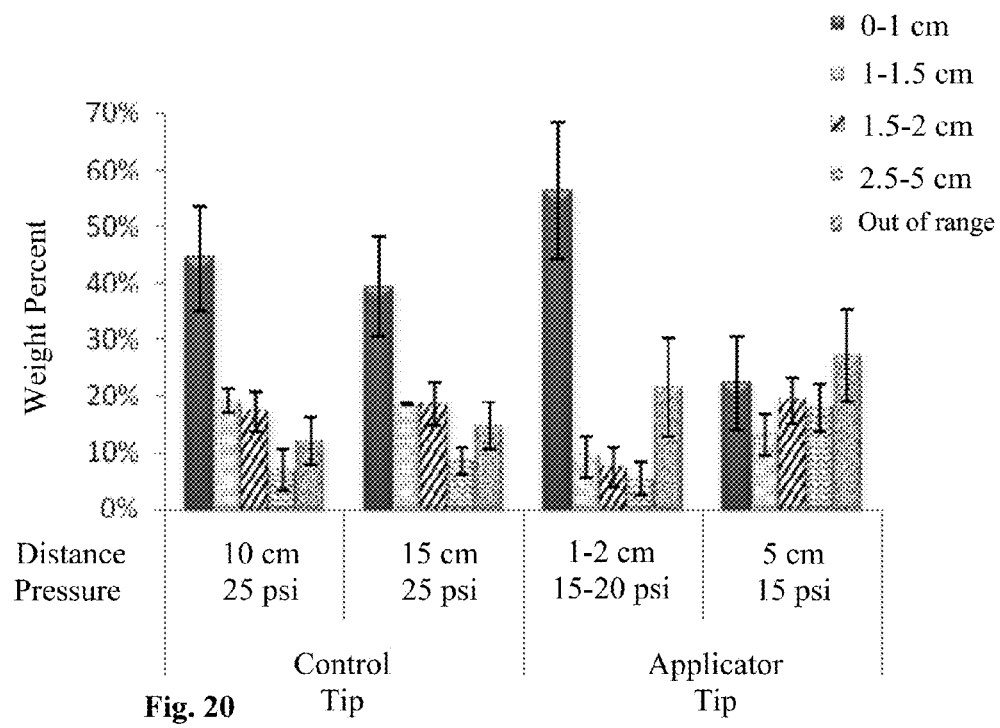
FIG. 20 shows the fibrin dispersion pattern around a center point following spraying with the applicator tip of one embodiment of the invention (as shown in FIG. 16) and the control tip, under the condition described in Example 8 below using the piled sheets shown in FIG. 19.

The results obtained are shown in FIG. 20. The out of range percentage weight seen in the graph is completion to the 100% clot weight.

In general, it was observed that spraying with the applicator tip according to the invention gave a different dispersion pattern at the different tested distances whereas spraying with the control tip resulted in the same dispersion pattern from both tested distances.

More specifically, spraying with the applicator tip according to the invention at a distance of 1-2 cm from the target resulted in an un-even dispersion of the sprayed material with accumulation of about 50% of the material in the 0-1 cm area (the 4 $cm^2$ sheet). In comparison, a distance of 5 cm from the target resulted in an even dispersion of the clot between the center point and the outer diameter of the 100 $cm^2$ sheet (each exposed sheet accumulated about 20% of the sprayed material).

Using the control tip for spraying from either distance (10 or 15 cm) resulted in an un-even dispersion of the sprayed material with accumulation of about 40% of the clot at the 0-1 cm distance (on the 4 $cm^2$ target area).

Advantageously, the applicator tip according to the invention enables both dispersion patterns enabling beneficial use for small and large targets.

Example 9

The Tridimensional Shape of the Spray Propelled from the Applicator Tip

In the following example the tridimensional shape of the spray (a broad cone vs. a narrow stream shape) was visually analyzed when using the applicator tip according to the invention. An applicator tip as illustrated in FIG. 16 was used, the above described control tip was used for comparison.

Spraying was carried out with 2.5 ml BAC2 and 2.5 ml thrombin. The applicator tip according to the invention was used at an inlet gas pressure of 20 psi, and the control tip was used at an inlet gas pressure of 25 psi.

It was observed (data not shown) that spraying with the applicator tip according to the invention resulted in formation of a broad cone-shaped spray starting at the nozzle orifices whereas spraying with the control tip formed a narrow-spray stream.

It appears that the wide spray angle (propelling a wide cone shape structure) formed when using the applicator tip according to the invention advantageously enables the beneficial coverage of both a small target (when spraying from a close distance to the target e.g. 1-2 cm) and a large target (when spraying from a larger distance to the target e.g. 5 cm) as seen in the previous example.

Example 10

Evaluation of the Targeting Quality of the Applicator Tip by Using the Migration Test Model In the following example, the targeting quality of the applicator tip according to the invention was evaluated by using the Migration Test Model. In this model, BAC2 and thrombin components are sprayed onto a target point located on a tilted plane, and the distance between the target point and the point where curing occurred and the components stopped migrating is measured. This distance is considered as the migration distance. Typically, when the migration distance of the two sprayed components is short and curing occurs on or close to the target point, the tip is considered as having a good targeting quality under the tested parameters (e.g. a specific inlet gas pressure and distance from the target).

For the testing, BAC2 and thrombin (each at a volume of 200 μl) were simultaneously sprayed onto a 90° tilted glass plane covered with a PVC sheet (the sheet was replaced following each testing), and the migration distance was measured. The fibrin sealant components were sprayed onto the surface by continually pressing the syringe's pistons at a rate of ~0.1 ml/sec. The spraying was carried out at an angle of 90° between the end of the tip and the target surface. The test was carried out with the applicator tip according to the invention and with the control tip. When using the applicator tip according to the invention (as shown in FIG. 16), spraying was carried out at a distance of 1-3 cm from the target and at an inlet gas pressure of 20 psi, and when using the control tip spraying was carried out at a distance of 1 or 10 cm (the recommended distance) and an inlet pressure of 25 psi. The results are shown in Table 8 below.

TABLE 8

The migration distance of the two components.

| | Applicator tip according to the invention (1-3 cm from target) *** | Control Tip (1 cm from target) ** | Control Tip (10 cm from target) ** |
|---|---|---|---|
| Migration Distance (cm) | 0.1 ± 0.25 (B) | 8.45 ± 1.00 (A) | 0.00 ± 0.00 (B) |

* Statistical analysis was carried out with ANOVA test, P Value between groups A, B is <0.01.
** N (replicates) for control tip = 4 and 5 when spraying was carried out from a distance of 1 and 10 cm from target, respectively.
*** N (replicates) for Applicator tip according to the invention = 10.

It was observed that spraying with the applicator tip according to the invention from a distance of 1-3 cm resulted in a short migration distance (0.1±0.25 cm) similar to the migration distance obtained when spraying with the control tip according to the recommended distance (10 cm from target). In comparison, using the control tip out of its recommended parameters (1 cm from the target) resulted in a long migration distance of 8.45±1.00.

These results show that spraying with the applicator tip according to the invention from a short distance e.g. 1-3 cm results in an efficient targeting.

Example 11

Effect of the Inlet Gas Pressure Level on the Mixing Quality of the Applicator Tip The following example was aimed to examine the effect of the inlet gas pressure level used during spraying on the mixing quality of an applicator tip according to the invention (as shown in FIG. 16). An inlet gas pressure in the range of 10 to 20 psi was tested.

Figure 21:
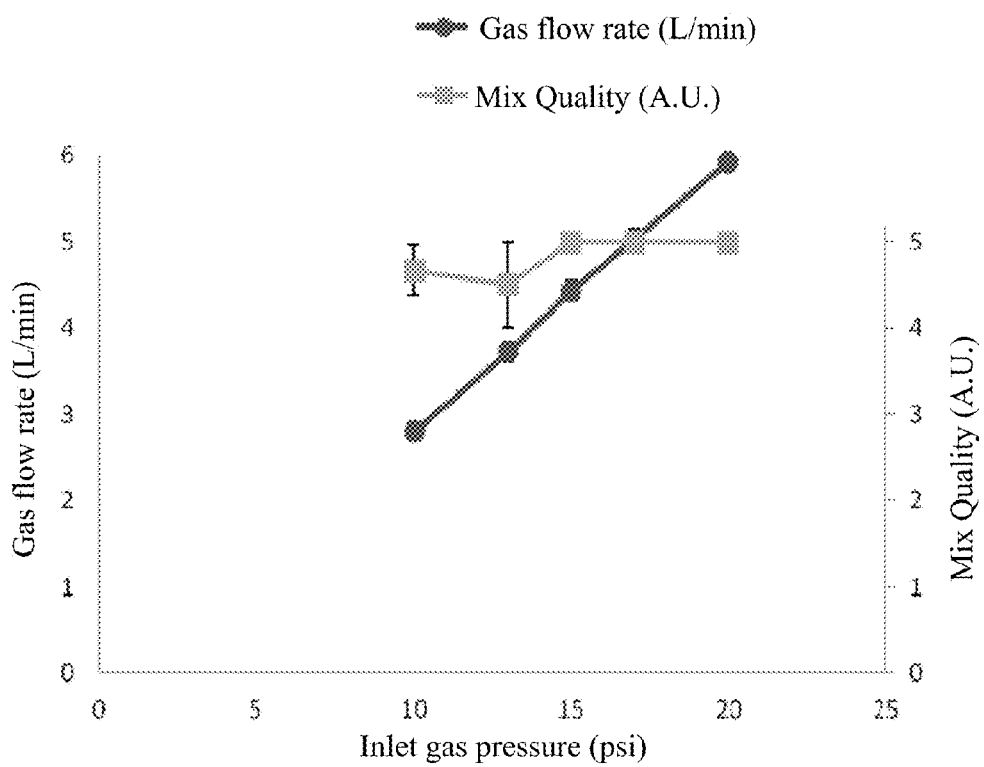
FIG. 21 shows the effect of the inlet gas pressure used during spraying on the mixing quality of the two fibrin sealant components when using the applicator tip according to one embodiment of the invention (as shown in FIG. 16). In parallel, the actual gas flow rate in the tip was measured using a flow meter.

For this experiment, 0.2 ml blue dyed thrombin and 0.2 ml yellow dyed BAC were sprayed from a distance of 1-2 cm from a target surface at an angle of 90° with respect to the target. The experiment was carried out in triplicates. Following spraying, the color of the obtained clot was visually evaluated according to the color ranking scale described in Example 2. In parallel, to understand the effect of the actual gas flow rate in the tip on the mixing quality, the gas flow rate was measured using a flow meter. The results are shown in FIG. 21.

It was observed that when spraying at a distance of 1-2 cm from the target with the applicator tip according to the invention, an inlet gas pressure of 15-20 psi and a gas flow of equal to 4.5 L/min and up to 6 L/min resulted in the optimal mixing.

Example 12

The Effect of the Fluids Conduits Arrangement on the Targeting Quality of the Applicator Tip in Dripping Application The above Examples evaluate the effect of the structure of the tip on its performance when application is carried out in spraying. In the following example, the effect of the fluids conduits arrangement on the applicator tip performance e.g. targeting quality is evaluated when application is carried out by dripping i.e. application without using a gas flow.

Two different design arrangements were examined: side by side fluid conduits (a bi-lumen arrangement) and concentric fluid conduits (see a frontal view of the fluid conduits arrangements in FIG. 17A—a bi-lumen arrangement; and FIG. 17B—a concentric arrangement). For this experiment, the applicator tip was constructed without the gas conduit.

Mixing quality was evaluated by using the Migration Test Model as elaborated in Example 10 above except that the glass plane was tilted 45° (and not 90° as above); application was carried out by dripping the components 1 cm from the glass plane; and no inlet gas pressure was used.

The fibrin sealant components were dripped onto the glass plane by continually pressing the syringe's pistons at a rate of ~0.1 ml/sec. Each arrangement was tested 10 times. Following clotting, the migration distance was measured. The results are shown in Table 9 below.

TABLE 9

The migration distance of the fibrin sealant components when dripping with the different fluid arrangements.

| | Arrangement design | |
|---|---|---|
| | Side by side | Concentric |
| Migration distance (cm) | 13.19 ± 2.29 | 8.42 ± 1.75 |

* Statistical analysis (t-test)—P Value < 0.05

It was observed that dripping the two components from a concentric lumen arrangement resulted in a shorter migration distance as compared to dripping the components from a side by side arrangement indicating that the concentric arrangement achieved better targeting quality under the tested parameters as compared to the targeting obtained when using the side by side arrangement.

Advantageously, in order to achieve an efficient targeting when using the tip according to the invention for dripping the liquid components, the fluid conduits can be arranged concentrically.

Example 13

The Efficacy of the Tip in an In-Vivo Model

The following experiments were aimed to examine the haemostatic performance of the applicator tip in an in-vivo model when used from a short distance from the target. The evaluation was carried out using two different models: the Rat kidney Hemorrhage Model and the Rabbit Hepatic Wound Model.

For this purpose, in the Rat Kidney Hemorrhage Model, the applicator tip (as in FIG. 16) was used from a close distance of 1-2 cm from the target and its efficacy was compared to the efficacy of the control applicator tip (described above) when used from a close distance of 2-3 cm (out of its recommended range). In the Rabbit Hepatic Wound Model the applicator tip (as in FIG. 16) was used from a close distance of 1-5 cm from the target and its efficacy was compared to the efficacy of the control applicator tip when used from a distance of 10-15 cm (according to the recommended instructions for use).

Rat Kidney Hemorrhage Model:

Experimental animals. Sprague Dawley albino rats, weighing 300-500 gr, were housed in an authorized facility according to the current ethical requirements. The health of each animal was ascertained and only overtly healthy animals were included in the experiment. Following receipt, the animals were subjected to an acclimation period of at least 5 days. The animals were provided ad libitum a commercial rodent diet and free access to drinking water.

Surgical procedure. Prior to the surgical procedure, the animal was anesthetized with an intraperitoneal injection of Pental (30-50 mg/kg). The animal's fur was then shaved on the left flank for the paralumbar laparotomy. The shaved site was wiped with alcohol. To maintain a temperature of 38-40° C., the rat was placed on a plastic cover deck, which was placed over a water bath preheated to 40° C. A thermo probe was inserted into the animal's rectum and the body temperature was monitored. The animal was positioned laterally and Sodium Heparin (2000 IU/Kg) was injected intravenously through the tail vein. A left paralumbar incision was made from the left hip to the twelfth rib, and the left kidney was exposed and separated from the perirenal fat. The rat was re-positioned to dorsal recumbence and allowed to stabilize for a period of five minutes or until the body temperature was utmost 39° C. The renal vessels were occluded with a soft vascular clamp and a gauze pad was tucked into the dorsal edge of the incision, between the exteriorized kidney and the incised abdominal wall, to absorb any blood or fluid shedding from the incision or from the abdominal cavity behind the kidney. A piece of transparent pre-cut plastic was placed on top of the gauze pad in order to direct the blood flow from the kidney into the pad. Another one or two squares of gauze were laid at the base of the plastic platform. A sagital heminephrectomy was carried out and the entire distal half of the kidney was removed perpendicular to the renal vessels. The cut surface (1.1-1.4 cm$^2$) of the removed section of the kidney was blotted three times on a piece of filter paper to measure the surface area of the excision. Each of the three kidney blots were traced, to aid in surface area determination.

Spray procedure. BAC and thrombin components were applied by spray onto the cut surface of the kidney using the applicator tip and the control tip—the spraying conditions are elaborated in Table 10 below. All applications were carried out at a continuous syringe hand press to supply a liquid flow of ~0.1-0.2 L/min of the components. A different tip was used for each animal.

The spraying was carried out as follows: the components were sprayed on the main area of the cut surface at an angle of 90° with respect to the surface with longitudinal movements over the entire cut surface. Following spraying, gauze pads were tucked around the cut kidney (without touching the formed fibrin clot) to absorb any blood from the cut area. Three minutes following spraying of the two components, the renal vessel clamp was released, and the kidney was observed for incidence of bleeding for a period of 30 minutes or until the animal expired (if the animal died, this animal was not included in the calculations). If bleeding through the fibrin clot was observed, the bleeding was gently absorbed with the gauze pad surrounding the kidney. Pads were replaced when needed, without touching the clot.

In order to evaluate whether the bleeding was stopped as a result of fibrin sealant spraying or as a result of auto-clotting of the animal's blood system (i.e. the heparinization did not work), the fibrin clot was removed using tweezers to assess bleeding severity from the kidney. Bleeding severity after clot removal was ranked as: severe, moderate or mild.

Euthanasia procedure. All animals were euthanized in a $CO_2$ chamber.

Blood loss calculation. The pads used to absorb the blood from the cut area were weighed and the net weight of the blood loss was calculated (by deducting the weight of the clean pads). The average blood loss of all tested rats for each tested group is shown in Table 10. The percentage of rats that did not bleed at all (zero blood loss) was also calculated and is shown in Table 10 below.

TABLE 10

The efficacy of the tip in a Rat Kidney Hemorrhage Model.

| Tip | Animals tested | Fibrin sealant volume applied (total ml) | Distance from target (cm) | Inlet gas pressure (psi) | Blood loss average ± STDEV (gr.)* | Percentage of rats that had no bleeding |
|---|---|---|---|---|---|---|
| Control tip | 3 | 0.6 | 2-3 | 25 | 2.22 ± 1.25 (A) | 0 |
| Applicator Tip | 8 | 0.6 | 1-2 | 15-20 | 0.00 ± 0.00 (B) | 100 |
| | 6 | 0.4 | 1-2 | 15 | 0.40 ± 0.98 (B) | 83 |

*Statistical analysis for "Blood loss average" was done with ANOVA test, p < 0.01 between the statistical groups A, B.

It was observed that using the applicator tip in the Rat Kidney Hemorrhage Model resulted in less blood loss and a higher percentage of non bleeding animals even when using a lower volume of fibrin sealant.

Observation of the bleeding severity showed that 1 rat in the control tip group had a moderate bleeding following clot removal and all the rest rats had severe bleeding indicating that any prevention in blood loss is as a result of the fibrin sealant haemostatic capabilities.

It was concluded that the applicator tip can be beneficially be used for stopping bleeding when spraying is carried from a close proximity to the target.

Rabbit Hepatic Wound Model:

In this model, monitoring of the animal was carried out 5-8 days post surgical procedure (a long term observation period enabling assessment of additional parameters—adhesion prevention and re-bleeding. Generally, the presence of fibrin sealant in surgical sites results in reduction of organ to organ adhesion at the operated area.

Also, in this model the blood supply to the cut area was not prevented and bleeding occurs immediately after the incision thus the Time to Hemostasis (the time elapsed from incision infliction until complete hemostasis occurred; TTH) was also evaluated as a short term parameter.

Experimental animals. New Zealand white rabbit (8 adult males; Harlan Laboratories, Jerusalem 91120, Israel) of known bacteriological and viral status, weighing 1.8-2.5 kg, were housed in an authorized facility according to the current ethical requirements. Following receipt, the health of each animal was ascertained and only overtly healthy animals were included in the experiment. The animals had free access to food and to sterilized tap water. The animals were subjected to an acclimation period of at 3-5 days. Surgical Procedure.

Each animal was weighed before the surgery and anesthetized with a solution (1 ml) of xylazine hydrochloride 20 mg/ml and ketamine 100 mg/ml by intramuscular injection. If the animal showed signs of awaking, the animal was also administered intravenously with a 0.2 ml ketamine (100 mg/ml).

Each animal was ventilated using a mask during the surgery. 5 IU/ml heparin was administered by a continuous infusion via the marginal ear vein at a rate of 60 ml/hour for 15 minutes prior to the surgical procedure. The skin of the abdominal area was shaved to be free of fur and scrubbed with a germicidal soap. The surgical site was disinfected with povidone iodine. Surgery was carried out using standard aseptic techniques. A median laparotomy was clipped, the liver was exposed and approximately 3-4 mm×30-40 mm of a liver lobe was excised. While maintained horizontally, the bleeding cut was wiped with a gauze pad.

Spray procedure. Following wiping the cut with the gauze pad, the cut area was sprayed with fibrin sealant using the applicator tip according to the invention at an inlet gas pressure of 15-20 psi from a close distance of 1-5 cm from the target. The applicator tip was tested on 5 animals. The control tip was sprayed at an inlet gas pressure of 25 psi, at a distance of 10 cm from the target (according to the instructions for use) and tested on 3 animals. All applications were carried out at angle of 90° while moving all over the cut area.

The spraying procedure was carried out in three stages:

Stage 1—application of 2 ml fibrin sealant (1 ml of each BAC and thrombin components) according to the conditions elaborated above. Following spraying, the sprayed site has been monitored for 30 seconds to note any bleeding;

Stage 2—application of 1 ml fibrin sealant (0.5 ml of each component) directly on bleeding points or evenly sprayed when there were several bleeding points. The site has been monitored for 30 seconds to note any bleeding;

Stage 3—application of 0.5 ml fibrin sealant (in total) directly on the remained bleeding points.

In each step the bleeding severity was evaluated (severe, moderate or mild) and the TTH (if occurred) was recorded for each animal (data not shown). Following the spraying procedures, the liver was carefully reinserted into the abdominal cavity and the muscular and superficial layers were sutured. The body temperature was verified and recorded before the animals were returned to their individual cages. All animals were continuously observed until recovery from surgery and examined at least twice a day. Animals were observed for any clinical abnormality once every workday following the day of surgery until the end of the experiment (5-8 days after surgery). After the observation period of 8 days, each animal was weighed, anesthetized and then sacrificed by an injection of barbiturate.

Necropsy procedure. The surgical site was re-cut and the liver was exposed. The hepatectomy site was observed for the presence of residual fibrin sealant which was qualitatively evaluated as small/moderate/significant amount. If possible, fibrin residuals were removed and weighed (see Table 11).

The presence and severity of surgical adhesions was evaluated according to the following grading: 0=no adhesions; 1=adhesion separated with minimal effort; 2=adhesion separated with moderate effort; and 3=adhesion separated with difficulty.

TABLE 11

Adhesion severity and fibrin clot residual amount after necropsy.

| Group | Exp. Period (days) | Animal Number | Residual Fibrin Sealant | Clot weight (mg) | Average clot weight* ± STDEV (mg) | Adhesion severity (0-3) |
|---|---|---|---|---|---|---|
| Applicator tip | 5 | 1 | Significant | 900.2 | 547.9 ± 294.8 | 0 |
| | 5 | 2 | Significant | — | | 0 |
| | 8 | 3 | Moderate | 195.9 | | 2** |
| | 8 | 4 | Significant | 627.6 | | 0 |
| | 8 | 5 | Significant | 467.9 | | 0 |
| Control tip | 5 | 1 | Significant | 597 | 717.8 ± 170.8 | 0 |
| | 8 | 2 | Small | — | | 0 |
| | 8 | 3 | Significant | 838.6 | | 0 |

*Statistical analysis - TTEST was done for "Average clot weight". No statistical significance was found between the applicator tip and the control tip.
**Adhesion site - Omentum to liver It was observed that using the applicator tip resulted in a mild-moderate bleeding severity after the first application stage whereas using the control tip resulted in a severe bleeding after the first application stage. Following the third stage of application, all tested tips (according to the invention and control) achieved complete hemostasis. The TTH obtained by using the applicator tip according to the invention was similar to that of the control tip (1 minute).

The efficacy of the applicator tip in spraying a fibrin sealant that effectively prevented adhesion was similar to that of the control tip. No significant difference was found in the rate of fibrin clot degradation between the two tips (as observed by the average clot weight at the end of the experiment). In all tested tips no re-bleeding occurred.

What is claimed is:

1. An applicator tip for spraying and/or mixing at least two fluids that react together, the tip comprising:
   at least two fluid conduits for carrying the at least two fluids, each conduit having at least one outlet opening, the openings are positioned substantially on a same plane;
   at least two gas conduits for carrying a gas volume, each gas conduit comprises a proximal gas tube and a distal gas tube, wherein each distal gas tube is bent as compared to the position of the proximal gas tube, and wherein each distal gas tube has one gas opening with a diameter, the gas openings positioned distal from the plane of the outlet openings; and
   a housing for accommodating the at least two fluid conduits and the at least two gas conduits
wherein the housing comprises a base plate from which the fluid conduits and the proximal gas tubes extend through and wherein the plane where the outlet openings are positioned, is elevated from the base plate by a conduit extension so that at least two recesses are formed between the conduit extension and the proximal gas tubes.

2. The tip according to claim 1, wherein the proximal and distal gas tubes are a one part unit.

3. The tip according to claim 1, wherein an axis of the distal gas tube forms an angle with respect to the plane of the outlet openings that is less than 90°.

4. The tip according to claim 3, wherein the angle is in the range of 15°-35°, 15°-25° or 15°-20°.

5. The tip according to claim 4, wherein the angle is about 20°.

6. The tip according to claim 3, wherein the axis of the distal gas tubes intersect at a common point located distal from the plane of the outlet openings.

7. The tip according to claim 1, wherein the ratio between a vertical distance from a center line of the tip to the gas opening and a vertical distance from the plane where the outlet openings are positioned to a center point of the gas opening is in the range of 0.8-1.75.

8. The tip according to claim 1, wherein the ratio between the vertical distance from the center line of the tip to the gas opening and the diameter of the gas opening is in the range 0.9-3.5 or in the range of 1-2.

9. The tip according to claim 1, wherein the diameter of the gas opening is in the range of higher than 0.4 to lower than 1.1 mm or in the range of 0.7-0.9 mm.

10. The tip according to claim 1, wherein the gas opening has an area in the range of higher than 0.125 $cm^2$ to lower than 0.950 $cm^2$ or in the range of 0.385 $cm^2$-0.636 cm2.

11. The tip according to claim 1, wherein the conduit extension is an elongation of the at least two fluid conduits.

12. The tip according to claim 1, wherein the ratio between a vertical distance from the plane where the outlet openings are positioned to a center point of the gas opening and a vertical distance from the base plate to the plane where the outlet openings are positioned is in the range of 0.19 to 0.50 or in the range of 0.235-0.400.

13. The tip according to claim 1, wherein the ratio between the vertical distance from the base plate to the plane where the outlet openings are positioned and a vertical distance from the base plate to a center point of the gas outlet opening is in the range of 0.71-0.81.

14. The tip according to claim 1, wherein the ratio between a vertical distance from the center line of the tip to the gas opening and the width of the recess is in the range of 2.5-14.

15. The tip according to claim 1, wherein the distance from the base plate to the plane where the outlet openings are positioned is in a range of 3.0-3.4 mm.

16. The tip according to claim 1, wherein the recess has a depth in a range of 3.0-3.4 mm.

17. The tip according to claim 1, wherein the recess has a width in a range of 0.10-0.40 mm.

18. The tip according to claim 17, comprising two fluid conduits arranged side by side, wherein the recess has a width in a range of 0.30-0.35 mm.

19. The tip according to claim 17, comprising two fluid conduits arranged concentrically, wherein the recess has a width in a range of 0.100-0.150 mm.

20. The tip according to claim 1, wherein the vertical distance from the base plate to a distant point of the tip is in the range of 4.0-5.0 mm.

21. The tip according to claim 1, wherein the overall diameter of the tip is in the range of 4.8-12 mm.

22. The tip according claim 1, wherein the housing comprises at least two structures for encapsulating at least a part of the gas conduit, wherein the structures emerge from the base plate.

23. The tip according to claim 1, wherein the housing comprises a structure for encapsulating the conduit extension.

24. The tip according to claim 1, wherein the housing comprises: i) at least two structures emerging from the base plate for encapsulating at least a part of the gas conduit, and ii) a structure for encapsulating the conduit extension, and wherein the recess is formed between the housing encapsulating the gas conduit and the housing encapsulating the conduit extension.

25. The tip according to claim 24, wherein the recess has a depth in a range of 3-3.4 mm.

26. The tip according to claim 24, wherein the recess has a width in a range of 0.10-0.40 mm.

27. The tip according to claim 26, comprising two fluid conduits arranged side by side, wherein the recess has a width in a range of 0.30-0.35 mm.

28. The tip according to claim 26, comprising two fluid conduits arranged concentrically, wherein the recess has a width in a range of 0.100-0.150 mm.

29. The tip according to claim 1, wherein the at least two fluid conduits are symmetrically arranged with respect to a center line of the tip.

30. The tip according to claim 1, comprising two fluid conduits arranged side by side.

31. The tip according to claim 1, comprising two fluid conduits arranged concentrically.

32. The tip according to claim 31, wherein one of the fluid conduits has two outlet openings and the other fluid conduit has one outlet opening.

33. The tip according to claim 1, wherein one of the fluids comprises thrombin and the other comprises fibrinogen.

34. The tip according to claim 1, for use at an inlet gas pressure in the range of 10-20 psi or in the range of 15-20 psi.

35. The tip according to claim 1, for use at an inlet gas flow in the range of 2.8 to 6 L/min or in the range of 4.4 to 6 L/min.

36. The tip according to claim 1, for use from a close proximity to a target spraying area, wherein the distance between the distant point of the tip and the target is less than 10 cm, less than 6 cm, in the range of 1-5 cm, 2-4 cm, 2-3 cm or in the range of 1-2 cm.

* * * * *